(12) United States Patent
Moreaux et al.

(10) Patent No.: US 10,174,380 B2
(45) Date of Patent: Jan. 8, 2019

(54) METHODS FOR PREDICTING MULTIPLE MYELOMA TREATMENT RESPONSE

(71) Applicants: INSERM (INSTITUT NATIONAL DE LA SANTE ET DE LA RECHERCHE MEDICALE), Paris (FR); UNIVERSITE DE MONTPELLIER, Montpellier (FR); CENTRE HOSPITALIER UNIVERSITAIRE DE MONTPELLIER, Montpellier (FR)

(72) Inventors: Jerome Moreaux, Montpellier (FR); Bernard Klein, Montpellier (FR)

(73) Assignees: INSERM (Institut National de la Sante et de la Recherche Medicale), Paris (FR); Universite de Montpellier, Montpellier (FR); Centre Hospitalier Universitaire de Montpellier, Montpellier (FR)

(*) Notice: Subject to any disclaimer, the term of this patent is extended or adjusted under 35 U.S.C. 154(b) by 0 days.

(21) Appl. No.: 14/433,681

(22) PCT Filed: Oct. 8, 2013

(86) PCT No.: PCT/EP2013/070964
§ 371 (c)(1),
(2) Date: Apr. 6, 2015

(87) PCT Pub. No.: WO2014/056928
PCT Pub. Date: Apr. 17, 2014

(65) Prior Publication Data
US 2015/0275305 A1    Oct. 1, 2015

(30) Foreign Application Priority Data
Oct. 8, 2012   (EP) .................................. 12306225

(51) Int. Cl.
| | | |
|---|---|---|
| *G01N 33/48* | (2006.01) |
| *C12Q 1/6886* | (2018.01) |
| *A61K 31/165* | (2006.01) |
| *A61K 31/185* | (2006.01) |
| *A61K 31/19* | (2006.01) |
| *A61K 31/4045* | (2006.01) |
| *G06F 19/20* | (2011.01) |
| *G06G 7/58* | (2006.01) |

(52) U.S. Cl.
CPC .......... *C12Q 1/6886* (2013.01); *A61K 31/165* (2013.01); *A61K 31/185* (2013.01); *A61K 31/19* (2013.01); *A61K 31/4045* (2013.01); *G06F 19/20* (2013.01); *C12Q 2600/106* (2013.01); *C12Q 2600/158* (2013.01); *C12Q 2600/16* (2013.01)

(58) Field of Classification Search
None
See application file for complete search history.

(56) References Cited

PUBLICATIONS

Moreaux et al., "A high-risk signature for patients with multiple myeloma established from the molecular classification of human myeloma cell lines", Haematologica, Dec. 20, 2010, pp. 574-580, vol. 96, No. 4.
Moreaux et al., "A High-risk signature for patients with multiple myeloma established from the molecular classification of human myeloma cell lines—supplementary appendix", Haematologica, Dec. 20, 2010, pp. 1-14.
Vanderkerken et al., "Epigenetic Changes of Myeloma Cells Within the Bone Marrow Microenvironment", Haematologic: Abstract Book 13th International Myeloma Workshop, May 1, 2011, pp. s8-s9.
Heller et al., "Genome-Wide Transcriptional Response to 5-Aza-2'-Deoxycytidine and Trichostatin A in Multiple Myeloma Cells", Cancer Research, Jan. 1, 2008, pp. 44-54, vol. 68, No. 1.
Smith et al., "The potential role of epigenetic therapy in multiple myeloma", British Journal of Haematology, Mar. 1, 2010, pp. 702-713, vol. 148, No. 5.
Nojima et al., "Genomic Screening for Genes Silenced by DNA Methylation Revealed an Association between RASD1 Inactivation and Dexamethasone Resistance in Multiple Myeloma", Clinical Cancer Research, Jul. 1, 2009, pp. 4356-4364, vol. 15, No. 13.

*Primary Examiner* — Eric S Dejong
(74) *Attorney, Agent, or Firm* — W & C IP

(57) ABSTRACT

The present invention relates to a method of testing whether a patient suffering of myeloma will respond or not to a histone deacetylase inhibitor (HDACi) comprising: determining the expression level (ELi) of several genes $G_1$-$G_n$ selected from table A in a biological sample obtained from said patient comparing the expression level (ELi) determined at step i) with a predetermined reference level (ELRi) iii) calculating the HAS score trough the following formula wherein βi represent the regression β coefficient reference value for the gene $G_i$ and Ci=1 if the expression of the gene $G_i$ (ELi) is higher than the predetermined reference level (ELRi) or Ci=−1 if the expression of the gene (ELi) is lower than or equal to the predetermined reference level (ELRi) comparing the score HAS determined at step iii) with a predetermined reference value $HAS_R$ v) and concluding that the patient will respond to the HDACi when the HAS score is higher than the predetermined reference value $HAS_R$ or concluding that the patient will not respond to the HDACi when the HAS score is lower than the predetermined value $HAS_R$.

Figure 1:
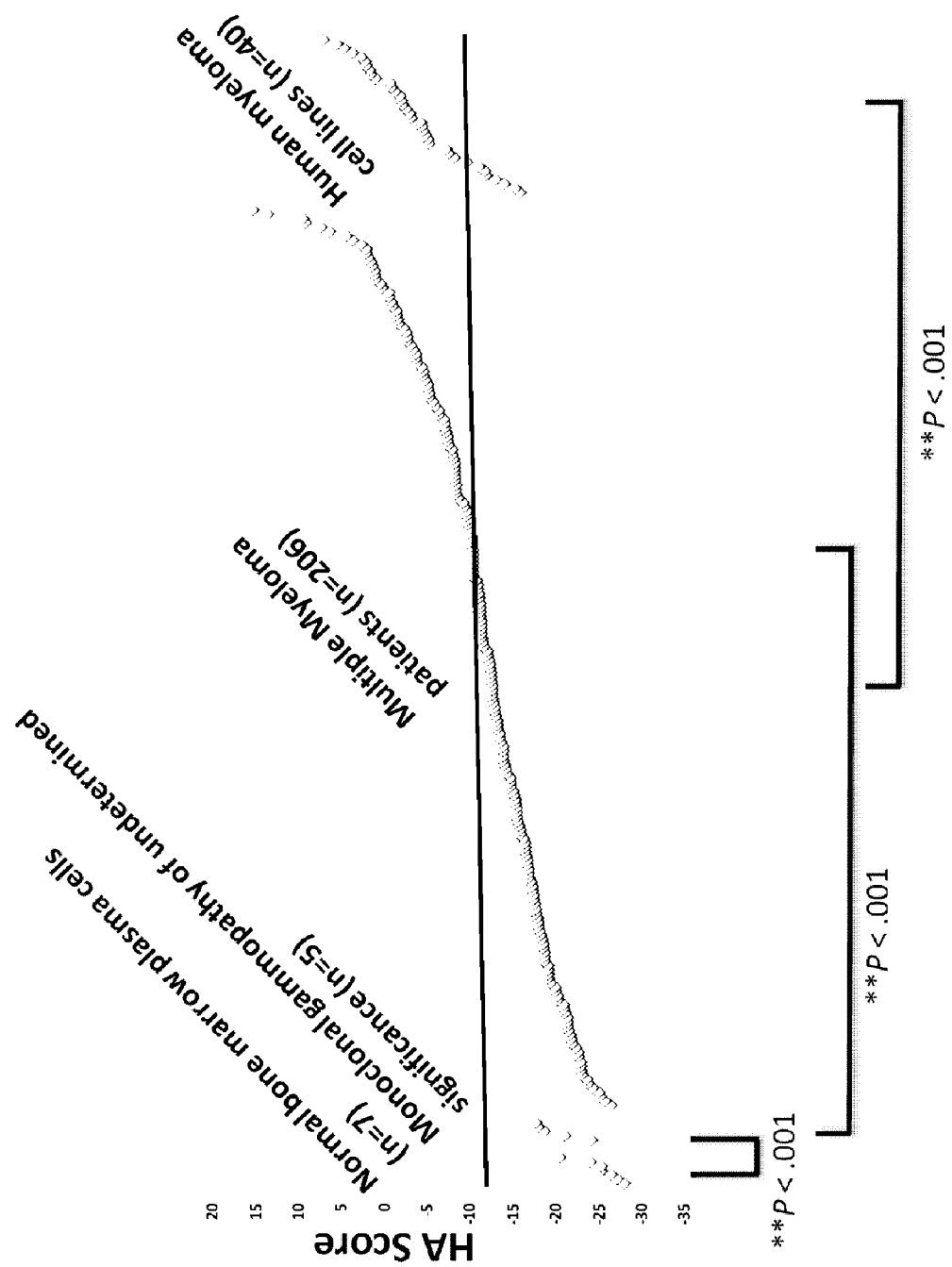

$$HAS = \sum_{i=1}^{n} \beta i \times Ci \qquad (I)$$

2 Claims, 7 Drawing Sheets

METHODS FOR PREDICTING MULTIPLE MYELOMA TREATMENT RESPONSE

FIELD OF THE INVENTION

The present invention relates to methods for predicting multiple myeloma treatment response.

BACKGROUND OF THE INVENTION

The molecular events governing the onset and progression of malignant transformation involve oncogenic activation and inactivation of tumor suppressor genes, which help cancer cells overriding the normal mechanisms controlling cellular survival and proliferation (1,2). These molecular events are triggered by genetic alterations (translocations, amplification, mutations) and also by epigenetic modifications (3). Epigenetic modifications include methylation of DNA cytosine residues and histone modifications and have been shown to be critical in the initiation and progression of many cancers (4). DNA methyltransferase inhibitors or HDAC inhibitors are now being used in the treatment of some hematologic malignancies including multiple myeloma (MM) and myelodysplastic syndromes (5-8). 18 different HDACs were identified and divided into four classes based on cellular localization and function (9). Class I includes HDACs 1, 2, 3 and 8, which are restrictively nuclear. Class II HDACs includes HDACs 4, 5, 7 and 9 (class IIa) shuttling back and forth between the nucleus and the cytoplasm and HDACs 6 and 10 (class IIb), with their distinctive two zinc-dependent catalytic sites, are expressed only in the cytoplasm. Class III contains the $NAD^+$ dependent sirtuin family, which does not act primarily on histones and class IV includes HDAC11 (9,10). Based on their chemical structure, HDACi can be grouped in four classes: hydroxamates (panobinostat, trichostatin-A (TSA), vorinostat, belinostat (PXD101), NVP-LAQ824 and givinostat (ITF2357)), cyclic peptide (romidepsin (depsipeptide)), aliphatic acids (valproic acid and sodium phenylbutyrate) and benzamides (MS-275, MGCD0103) (10). HDACi are characterized as class I-specific HDACs inhibitors (MGCD0103, romidepsin and MS-275) or as pan-HDAC inhibitors, denoting activity against both classes I and II HDACs (TSA, panobinostat, vorinostat and belinostat) (10). Multiple myeloma is a plasma cell neoplasm characterized by the accumulation of malignant plasma cells (PCs), termed Multiple Myeloma Cells (MMCs) within the bone marrow (BM). Despite the recent introduction of new therapies such as Lenalidomide and Bortezomib, MM remains an almost incurable disease. MM arises through the accumulation of multiple genetic changes that include an aberrant or overexpression of a D-type cyclin gene, cyclin D1 (CCND1) in the case of t(11; 14) translocation or gain in 11q13, cyclin D3 (CCND3) in the case of the rare t(6; 14) translocation, or cyclin D2 (CCND2) on the background of a translocation involving c-maf (t(14; 16)) or MMSET/FGFR3 (t(4; 14)) (11,12). HDACi have already been evaluated in MM including Trichostatin A (TSA) (13), vorinostat (14,15), NVP-LAQ824 (16), depsipeptide (17), KD5170 (18), valproic acid (19, 20) and panobinostat (10). In MM, HDACi induce G1 cell cycle arrest by enhancing expression of p21, p53 and dephosphorylation of Rb (13, 15, 20), induce apoptosis by downregulation of Bcl-2 family members (15,17) and overcome drug resistance mediated by the bone marrow environment (15). Clinical trials were designed to analyze the activity of HDACi as single agents in Phase I/II trials in relapsed/refractory MM patients. When used as single agent, HDACi had modest activity (21,22), but in combination with other anti-MM treatments, they can induce durable responses (23,24).

The identification of biomarkers predictive for sensitivity of MMCs to HDACi is an important objective for optimizing these clinical trials. In the present invention, the inventors used gene expression profiling of Multiple Myeloma Cells (MMCs) to build a novel "histone acetylation gene expression score" that makes it possible identification of patients whose MMCs will be targeted by HDAC inhibition.

SUMMARY OF THE INVENTION

The present invention relates to a method of testing whether a patient suffering of multiple myeloma will respond or not to a histone deacetylase inhibitor (HDACi).

DETAILED DESCRIPTION OF THE INVENTION

The multiple myeloma treatment response was investigated by the inventors using histone deacetylase inhibitor (HDACi) and human multiple myeloma cell lines. The inventors analyzed gene expression profiles of 5 MM cells lines treated with trichostatin A (TSA). 95 genes were deregulated by TSA and 37 out of 95 TSA deregulated genes have prognostic value in a cohort of 206 newly-diagnosed MM patients. The inventors also built a histone acetylation scores (HA Score or HAS) using the probe set signal value weighted by the beta coefficient of prognostic genes. The HA Score is predictive for myeloma cells HDACi sensitivity of HMCL and primary myeloma cells in vitro. The HA Score allows identification of myeloma patients that could benefit HDAC inhibitor treatment.

Definitions

The term "patient" denotes a mammal. In a preferred embodiment of the invention, a patient refers to any patient (preferably human) afflicted with multiple myeloma. The term "multiple myeloma" refers to multiple myeloma such as revised in the World Health Organisation Classification C90.

The term "histone deacetylase inhibitor" or "HDACi" has its general meaning in the art and refers to a multiple myeloma treatment. The term "histone deacetylase inhibitor" or "HDACi" refers to histone deacetylase inhibitor that can be grouped in four classes: hydroxamates (panobinostat (LBH-589), trichostatin-A (TSA), vorinostat (SAHA), belinostat (PXD101), NVP-LAQ824 and givinostat (ITF2357)), cyclic peptide (romidepsin (depsipeptide)), aliphatic acids (valproic acid (VPA) and sodium phenylbutyrate) and benzamides (MS-275, MGCD0103) (10). HDACi are characterized as class I-specific HDACs inhibitors (MGCD0103, romidepsin and MS-275) or as pan-HDAC inhibitors, denoting activity against both classes I and II HDACs (TSA, panobinostat, vorinostat and belinostat) (10).

The term "biological sample" refers to multiple myeloma cells, bone marrow or medullary cell.

All the genes pertaining to the invention are known per se, and are listed in the below Table A.

TABLE A

Set of predictive genes.

| Gene | Gene Symbol | Gene name | Gene ID | β coefficient | Reference level (ELRi) |
|---|---|---|---|---|---|
| G1 | SCN3A | sodium channel, voltage-gated, type III, alpha subunit | 210432_s_at | 0.996958090200582 | 64.0776699029126 |
| G2 | ANK3 | ankyrin 3 | 206385_s_at | −0.913919887371127 | 81.0679611650485 |
| G3 | APLP2 | amyloid beta (A4) precursor-like protein 2 | 214875_x_at | 0.784702839669874 | 24.7572815533981 |
| G4 | QKI | quaking homolog, KH domain RNA binding | 212636_at | −0.804915153416405 | 85.4368932038835 |
| G5 | SYT11 | synaptotagmin XI | 209198_s_at | −0.71983191352392 | 38.8349514563107 |
| G6 | KIAA1324L | KIAA1324-like | 235301_at | −0.921569046866849 | 87.864077669903 |
| G7 | DHRS2 | dehydrogenase/reductase (SDR family) member 2 | 214079_at | 1.13644894957913 | 10.6796116504854 |
| G8 | DFNA5 | deafness, autosomal dominant 5 | 203695_s_at | −0.601888717627172 | 48.5436893203884 |
| G9 | STAT1 | signal transducer and activator of transcription 1 | 209969_s_at | 0.865200607771322 | 20.873786407767 |
| G10 | SERPINI1 | serpin peptidase inhibitor, clade I (neuroserpin), member 1 | 205352_at | 0.708779268580762 | 55.3398058252427 |
| G11 | BBS9 or PTHB1 | Bardet-Biedl syndrome 9 or parathyroid hormone-responsive B1 | 209958_s_at | 0.854129984250074 | 28.1553398058252 |
| G12 | RGS1 | regulator of G-protein signaling 1 | 216834_at | −0.604322500555556 | 65.5339805825243 |
| G13 | HLA-DPA1 | major histocompatibility complex, class II, DP alpha 1 | 211990_at | −0.708484927244178 | 79.126213592233 |
| G14 | FN1 | fibronectin 1 | 212464_s_at | −0.988700830206777 | 90.2912621359223 |
| G15 | KLHL24 | kelch-like 24 | 226158_at | 1.23690256697662 | 78.1553398058252 |
| G16 | HLA-DRA | major histocompatibility complex, class II, DR alpha | 208894_at | −1.02237505806332 | 33.9805825242718 |
| G17 | PTPRG | protein tyrosine phosphatase, receptor type, G | 204944_at | 0.749927151477102 | 16.9902912621359 |
| G18 | RASGEF1B | RasGEF domain family; member 1B | 230233_at | −0.855660771294511 | 89.3203883495146 |
| G19 | OAS1 | 2',5'-oligoadenylate synthetase 1 | 205552_s_at | 0.918506668310864 | 69.9029126213592 |
| G20 | TRIM38 | tripartite motif-containing 38 | 203567_s_at | 0.673917187650873 | 15.5339805825243 |
| G21 | SERPINB1 | Serpin peptidase inhibitor; clade B (ovalbumin); member 1 | 228726_at | −0.96828128571625 | 87.378640776699 |
| G22 | TRPS1 | trichorhinophalangeal syndrome I | 222651_s_at | 0.776522209484358 | 13.1067961165049 |
| G23 | CFHR1 or CFHL1 | complement factor H-related 1 | 215388_s_at | −0.644744853140614 | 77.1844660194175 |
| G24 | PHLDA1 | pleckstrin homology-like domain, family A, member 1 | 225842_at | −1.14097033702181 | 89.8058252427184 |
| G25 | HLA-DQB1 | major histocompatibility complex, class II, DQ beta 1 | 212998_x_at | −0.741541655889151 | 76.2135922330097 |
| G26 | SELL | selectin L | 204563_at | 0.665456120458623 | 75.7281553398058 |
| G27 | HLA-DRB1 | major histocompatibility complex; class II; DR beta 1 | 215193_x_at | −0.835746441816605 | 88.8349514563107 |

TABLE A-continued

Set of predictive genes.

| Gene | Gene Symbol | Gene name | Gene ID | β coefficient | Reference level (ELRi) |
|---|---|---|---|---|---|
| G28 | NFKBIZ | nuclear factor of kappa light polypeptide gene enhancer in B-cells inhibitor, zeta | 223218_s_at | −0.7451541815469 | 79.126213592233 |
| G29 | PARP14 | poly (ADP-ribose) polymerase family, member 14 | 224701_at | 1.08062305938478 | 10.1941747572816 |
| G30 | CFI | complement factor I | 203854_at | 0.85259982594094 | 10.6796116504854 |
| G31 | MAN1C1 | mannosidase, alpha, class 1C, member 1 | 218918_at | −0.709223593142427 | 33.495145631068 |
| G32 | BASP1 | brain abundant, membrane attached signal protein 1 | 202391_at | −0.9921976055676 | 83.495145631068 |
| G33 | GDAP1 | ganglioside-induced differentiation-associated protein 1 | 226269_at | 0.988539786187137 | 62.621359223301 |
| G34 | EFHC1 | EF-hand domain (C-terminal) containing 1 | 219833_s_at | −0.587820758510972 | 51.9417475728155 |
| G35 | ANXA1 | annexin A1 | 201012_at | 0.699836394397964 | 25.7281553398058 |
| G36 | RTN2 | reticulon 2 | 34408_at | −1.25994066884418 | 36.4077669902913 |
| G37 | DDX60L or FLJ31033 | DEAD (Asp-Glu-Ala-Asp) box polypeptide 60-like | 228152_s_at | −0.629835803277543 | 54.8543689320388 |

Methods for Predicting Response

The present invention relates to a method of testing whether a patient suffering of multiple myeloma will respond or not to a histone deacetylase inhibitor (HDACi) comprising:
  i) determining the expression level (ELi) of several genes $G_1$-$G_n$ selected from table A in a biological sample obtained from said patient
  ii) comparing the expression level (ELi) determined at step i) with a predetermined reference level (ELRi)
  iii) calculating the HAS score trough the following formula $$HAS = \sum_{i=1}^{n} \beta i \times Ci$$

wherein βi represent the regression coefficient reference value for the gene $G_i$ and Ci=1 if the expression of the gene $G_i$ (ELi) is higher than the predetermined reference level (ELRi) or Ci=−1 if the expression of the gene (ELi) is lower than or equal to the predetermined reference level (ELRi)
  iv) comparing the score HAS determined at step iii) with a predetermined reference value $HAS_R$
  v) and concluding that the patient will respond to the HDACi when the HAS score is higher than the predetermined reference value $HAS_R$ or concluding that the patient will not respond to the HDACi when the HAS score is lower than the predetermined reference value $HAS_R$ In some embodiments, the levels of at least 34 genes from Table A are determined wherein said genes are: SCN3A, ANK3, APLP2, QKI, SYT11, KIAA1324L, DHRS2, DFNA5, STAT1, SERPINI1, BBS9 (or PTHB1), RGS1, HLA-DPA1, FN1, KLHL24, HLA-DRA, PTPRG, RASGEF1B, OAS1, TRIM38, SERPINB1, TRPS1, CFHR1 (or CFHL1), PHLDA1, HLA-DQB1, SELL, HLA-DRB1, NFKBIZ, PARP14, CFI, MAN1C1, BASP1, GDAP1 and EFHC1.

In some embodiment, the level of 34, 35, 36, or 37 genes from Table A are determined wherein every combinations of genes comprises a minimal set of 34 genes consisting of: SCN3A, ANK3, APLP2, QKI, SYT11, KIAA1324L, DHRS2, DFNA5, STAT1, SERPINI1, BBS9 (or PTHB1), RGS1, HLA-DPA1, FN1, KLHL24, HLA-DRA, PTPRG, RASGEF1B, OAS1, TRIM38, SERPINB1, TRPS1, CFHR1 (or CFHL1), PHLDA1, HLA-DQB1, SELL, HLA-DRB1, NFKBIZ, PARP14, CFI, MAN1C1, BASP1, GDAP1 and EFHC1.

In some embodiment, the level of 35 genes from Table A are determined wherein said genes are:
  SCN3A, ANK3, APLP2, QKI, SYT11, KIAA1324L, DHRS2, DFNA5, STAT1, SERPINI1, BBS9 (or PTHB1), RGS1, HLA-DPA1, FN1, KLHL24, HLA-DRA, PTPRG, RASGEF1B, OAS1, TRIM38, SERPINB1, TRPS1, CFHR1 (or CFHL1), PHLDA1, HLA-DQB1, SELL, HLA-DRB1, NFKBIZ, PARP14, CFI, MAN1C1, BASP1, GDAP1, EFHC1, and ANXA1, or,
  SCN3A, ANK3, APLP2, QKI, SYT11, KIAA1324L, DHRS2, DFNA5, STAT1, SERPINI1, BBS9 (or PTHB1), RGS1, HLA-DPA1, FN1, KLHL24, HLA-DRA, PTPRG, RASGEF1B, OAS1, TRIM38, SERPINB1, TRPS1, CFHR1 (or CFHL1), PHLDA1, HLA-DQB1, SELL, HLA-DRB1, NFKBIZ, PARP14, CFI, MAN1C1, BASP1, GDAP1, EFHC1, and RTN2, or,
  SCN3A, ANK3, APLP2, QKI, SYT11, KIAA1324L, DHRS2, DFNA5, STAT1, SERPINI1, BBS9 (or PTHB1), RGS1, HLA-DPA1, FN1, KLHL24, HLA-DRA, PTPRG, RASGEF1B, OAS1, TRIM38, SERPINB1, TRPS1, CFHR1 (or CFHL1), PHLDA1, HLA-DQB1, SELL, HLA-DRB1, NFKBIZ, PARP14, CFI, MAN1C1, BASP1, GDAP1, EFHC1, and DDX60L (FLJ31033).

In some embodiment, the level of 36 genes from Table A are determined wherein said genes are:

SCN3A, ANK3, APLP2, QKI, SYT11, KIAA1324L, DHRS2, DFNA5, STAT1, SERPINI1, BBS9 (or PTHB1), RGS1, HLA-DPA1, FN1, KLHL24, HLA-DRA, PTPRG, RASGEF1B, OAS1, TRIM38, SERPINB1, TRPS1, CFHR1 (or CFHL1), PHLDA1, HLA-DQB1, SELL, HLA-DRB1, NFKBIZ, PARP14, CFI, MAN1C1, BASP1, GDAP1, EFHC1, ANXA1, and RTN2, or, SCN3A, ANK3, APLP2, QKI, SYT11, KIAA1324L, DHRS2, DFNA5, STAT1, SERPINI1, BBS9 (or PTHB1), RGS1, HLA-DPA1, FN1, KLHL24, HLA-DRA, PTPRG, RASGEF1B, OAS1, TRIM38, SERPINB1, TRPS1, CFHR1 (or CFHL1), PHLDA1, HLA-DQB1, SELL, HLA-DRB1, NFKBIZ, PARP14, CFI, MAN1C1, BASP1, GDAP1, EFHC1, ANXA1, and DDX60L (FLJ31033), or, SCN3A, ANK3, APLP2, QKI, SYT11, KIAA1324L, DHRS2, DFNA5, STAT1, SERPINI1, BBS9 (or PTHB1), RGS1, HLA-DPA1, FN1, KLHL24, HLA-DRA, PTPRG, RASGEF1B, OAS1, TRIM38, SERPINB1, TRPS1, CFHR1 (or CFHL1), PHLDA1, HLA-DQB1, SELL, HLA-DRB1, NFKBIZ, PARP14, CFI, MAN1C1, BASP1, GDAP1, EFHC1, RTN2, and DDX60L (FLJ31033).

In some embodiments, the level of the 37 genes of Table A are determined.

Determination of the expression level of the genes can be performed by a variety of techniques. Generally, the expression level as determined is a relative expression level. More preferably, the determination comprises contacting the biological sample with selective reagents such as probes, primers or ligands, and thereby detecting the presence, or measuring the amount, of polypeptide or nucleic acids of interest originally in the biological sample. Contacting may be performed in any suitable device, such as a plate, microtiter dish, test tube, well, glass, column, and so forth. In specific embodiments, the contacting is performed on a substrate coated with the reagent, such as a nucleic acid array or a specific ligand array. The substrate may be a solid or semi-solid substrate such as any suitable support comprising glass, plastic, nylon, paper, metal, polymers and the like. The substrate may be of various forms and sizes, such as a slide, a membrane, a bead, a column, a gel, etc. The contacting may be made under any condition suitable for a detectable complex, such as a nucleic acid hybrid or an antibody-antigen complex, to be formed between the reagent and the nucleic acids or polypeptides of the biological sample.

In a preferred embodiment, the expression level may be determined by determining the quantity of mRNA.

Methods for determining the quantity of mRNA are well known in the art. For example the nucleic acid contained in the biological sample is first extracted according to standard methods, for example using lytic enzymes or chemical solutions or extracted by nucleic-acid-binding resins following the manufacturer's instructions. The extracted mRNA is then detected by hybridization (e. g., Northern blot analysis) and/or amplification (e.g., RT-PCR). Preferably quantitative or semi-quantitative RT-PCR is preferred. Real-time quantitative or semi-quantitative RT-PCR is particularly advantageous.

Other methods of amplification include ligase chain reaction (LCR), transcription-mediated amplification (TMA), strand displacement amplification (SDA) and nucleic acid sequence based amplification (NASBA).

Nucleic acids having at least 10 nucleotides and exhibiting sequence complementarity or homology to the mRNA of interest herein find utility as hybridization probes or amplification primers. It is understood that such nucleic acids need not be identical, but are typically at least about 80% identical to the homologous region of comparable size, more preferably 85% identical and even more preferably 90-95% identical. In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e.g. avidin/biotin).

Probes typically comprise single-stranded nucleic acids of between 10 to 1000 nucleotides in length, for instance of between 10 and 800, more preferably of between 15 and 700, typically of between 20 and 500. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e. they preferably hybridize under high stringency hybridization conditions (corresponding to the highest melting temperature Tm, e.g., 50% formamide, 5× or 6×SCC. SCC is a 0.15 M NaCl, 0.015 M Na-citrate).

The nucleic acid primers or probes used in the above amplification and detection method may be assembled as a kit. Such a kit includes consensus primers and molecular probes. A preferred kit also includes the components necessary to determine if amplification has occurred. The kit may also include, for example, PCR buffers and enzymes; positive control sequences, reaction control primers; and instructions for amplifying and detecting the specific sequences.

In a particular embodiment, the methods of the invention comprise the steps of providing total RNAs extracted from a biological samples and subjecting the RNAs to amplification and hybridization to specific probes, more particularly by means of a quantitative or semi-quantitative RT-PCR.

In another preferred embodiment, the expression level is determined by DNA chip analysis. Such DNA chip or nucleic acid microarray consists of different nucleic acid probes that are chemically attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes comprise nucleic acids such as cDNAs or oligonucleotides that may be about 10 to about 60 base pairs. To determine the expression level, a biological sample from a test patient, optionally first subjected to a reverse transcription, is labelled and contacted with the microarray in hybridization conditions, leading to the formation of complexes between target nucleic acids that are complementary to probe sequences attached to the microarray surface. The labelled hybridized complexes are then detected and can be quantified or semi-quantified. Labelling may be achieved by various methods, e.g. by using radioactive or fluorescent labelling. Many variants of the microarray hybridization technology are available to the man skilled in the art (see e.g. the review by Hoheisel, Nature Reviews, Genetics, 2006, 7:200-210)

In this context, the invention further provides a DNA chip comprising a solid support which carries nucleic acids that are specific to the genes listed in Table A.

Predetermined reference values ELRi or $HAS_R$ used for comparison may consist of "cut-off" values.

For example; each reference ("cut-off") value ELRi for each gene may be determined by carrying out a method comprising the steps of:

a) providing a collection of samples from patients suffering of multiple myeloma;

b) determining the expression level of the relevant gene for each sample contained in the collection provided at step a);

c) ranking the samples according to said expression level d) classifying said samples in pairs of subsets of increasing, respectively decreasing, number of members ranked according to their expression level, e) providing, for each sample provided at step a), information relating to the actual clinical outcome for the corresponding cancer patient (i.e. the duration of the disease-free survival (DFS) or the overall survival (OS) or both);

f) for each pair of subsets of tumour tissue samples, obtaining a Kaplan Meier percentage of survival curve;

g) for each pair of subsets of tumour tissue samples calculating the statistical significance (p value) between both subsets h) selecting as reference value ELR for the expression level, the value of expression level for which the p value is the smallest.

For example the expression level of a gene Gi has been assessed for 100 samples of 100 patients. The 100 samples are ranked according to the expression level of gene Gi. Sample 1 has the highest expression level and sample 100 has the lowest expression level. A first grouping provides two subsets: on one side sample Nr 1 and on the other side the 99 other samples. The next grouping provides on one side samples 1 and 2 and on the other side the 98 remaining samples etc., until the last grouping: on one side samples 1 to 99 and on the other side sample Nr 100. According to the information relating to the actual clinical outcome for the corresponding cancer patient, Kaplan Meier curves are prepared for each of the 99 groups of two subsets. Also for each of the 99 groups, the p value between both subsets was calculated. The reference value ELRi is then selected such as the discrimination based on the criterion of the minimum p value is the strongest. In other terms, the expression level corresponding to the boundary between both subsets for which the p value is minimum is considered as the reference value. It should be noted that according to the experiments made by the inventors, the reference value ELRi is not necessarily the median value of expression levels.

The man skilled in the art also understands that the same technique of assessment of the $HAS_R$ could be used for obtaining the reference value and thereafter for assessment of the response to HDACi. However in one embodiment, the reference value $HAS_R$ is the median value of HAS.

In one embodiment, the reference value ELRi for the genes are described in table A (right column).

Typically, the reference value $HAS_R$ is −11.3 for determining whether a patient suffering of multiple myeloma will respond to an HDACi and for predicting the survival time of patient suffering of multiple myeloma.

Typically, the reference value $HAS_R$ is −12.3 for determining whether a patient suffering of multiple myeloma will respond to an HDACi.

The regression β coefficient reference values may be easily determined by the skilled man in the art for each gene using a Cox model. The Cox model is based on a modeling approach to the analysis of survival data. The purpose of the model is to simultaneously explore the effects of several variables on survival. The Cox model is a well-recognised statistical technique for analysing survival data. When it is used to analyse the survival of patients in a clinical trial, the model allows us to isolate the effects of treatment from the effects of other variables. The logrank test cannot be used to explore (and adjust for) the effects of several variables, such as age and disease duration, known to affect survival. Adjustment for variables that are known to affect survival may improve the precision with which we can estimate the treatment effect. The regression method introduced by Cox is used to investigate several variables at a time. It is also known as proportional hazards regression analysis. Briefly, the procedure models or regresses the survival times (or more specifically, the so-called hazard function) on the explanatory variables. The hazard function is the probability that an individual will experience an event (for example, death) within a small time interval, given that the individual has survived up to the beginning of the interval. It can therefore be interpreted as the risk of dying at time t. The quantity h0 (t) is the baseline or underlying hazard function and corresponds to the probability of dying (or reaching an event) when all the explanatory variables are zero. The baseline hazard function is analogous to the intercept in ordinary regression (since exp0=1). The regression coefficient β gives the proportional change that can be expected in the hazard, related to changes in the explanatory variables. The coefficient β is estimated by a statistical method called maximum likelihood. In survival analysis, the hazard ratio (HR) (Hazard Ratio=exp(β)) is the ratio of the hazard rates corresponding to the conditions described by two sets of explanatory variables. For example, in a drug study, the treated population may die at twice the rate per unit time as the control population. The hazard ratio would be 2, indicating higher hazard of death from the treatment.

In one embodiment, the regression β coefficient reference values are described in Table A.

The invention also relates to a kit for performing the methods as above described, wherein said kit comprises means for measuring the expression level of the genes listed in Table A. Typically the kit may include a primer, a set of primers, a probe, a set of probes as above described. In a particular embodiment, the probe or set of probes are labelled as above described. The kit may also contain other suitably packaged reagents and materials needed for the particular detection protocol, including solid-phase matrices, if applicable, and standards.

In a particular embodiment, the score may be generated by a computer program.

Methods of Treatment

The method of the invention allows to define a subgroup of patients who will be responsive ("responder") or not ("non responder") to the treatment with a histone deacetylase inhibitor.

A further object of the invention relates to a method for the treatment of multiple myeloma in a patient in need thereof.

In the context of the invention, the term "treating" or "treatment", as used herein, means reversing, alleviating, inhibiting the progress of, or preventing the disorder or condition to which such term applies, or one or more symptoms of such disorder or condition.

In a particular embodiment, the method comprises the following steps a) testing whether the patient will respond or not to a histone deacetylase inhibitor (HDACi) by performing the method according to the invention b) administering the histone deacetylase inhibitor, if said patient has as score higher than the reference value $HAS_R$ (i.e. the patient will respond to the histone deacetylase inhibitor).

A further object of the invention relates to a histone deacetylase inhibitor for use in the treatment of multiple myeloma in a patient in need thereof, wherein the patient was being classified as responder by the method as above described.

The invention will be further illustrated by the following figures and examples. However, these examples and figures should not be interpreted in any way as limiting the scope of the present invention.

FIGURES

FIG. 1: Histone acetylation Score in normal and malignant plasma cells

Histone acetylation Score in normal bone marrow plasma cells (N=7), in premalignant plasma cells of patients with monoclonal gammopathy of undetermined significance (MGUS, N=5), in multiple myeloma cells of patients with intramedullary MM (N=206) and in human myeloma cell lines (N=40). ** Indicate that the score value is significantly different with a P value<0.01.

Figure 2:
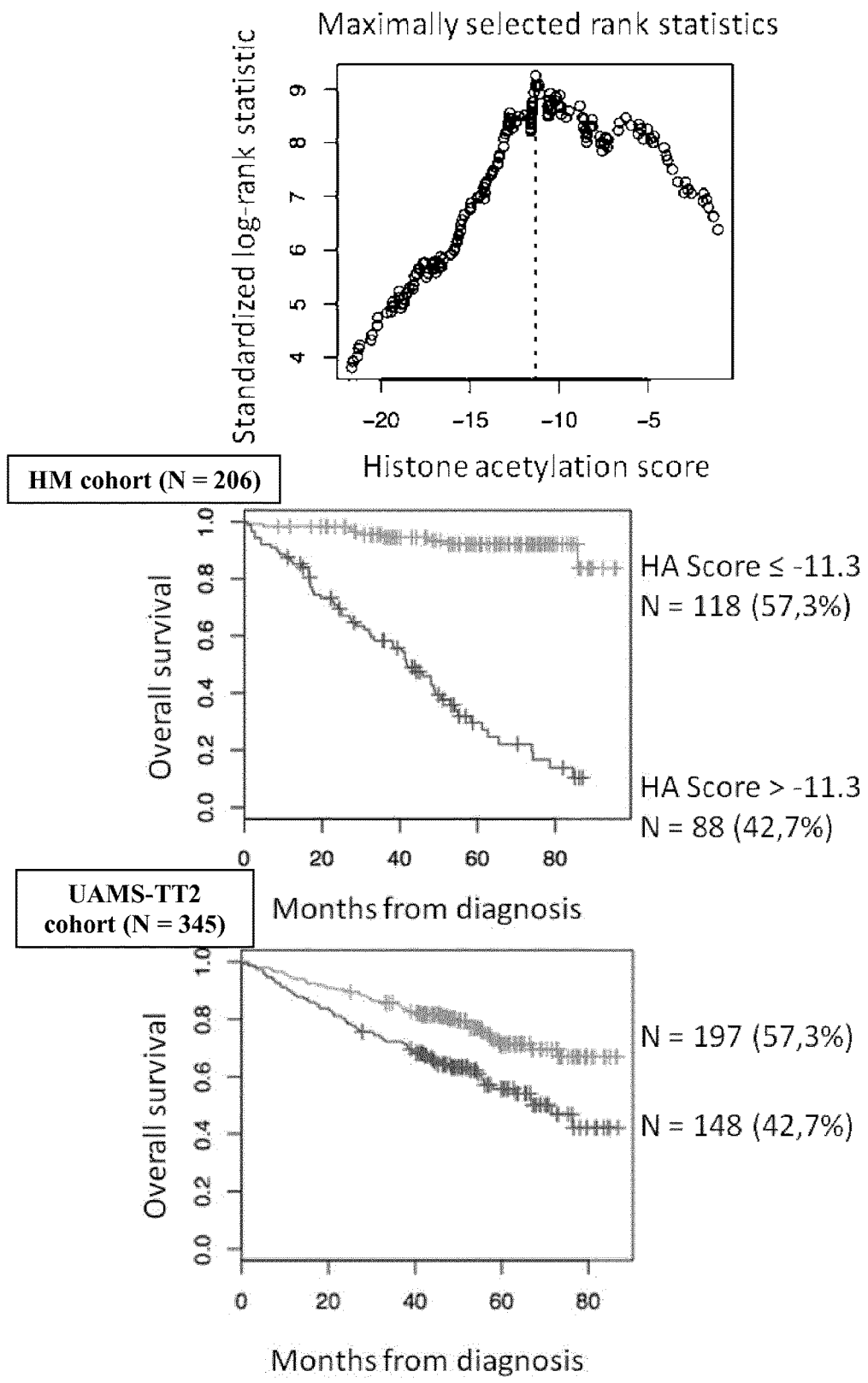

FIG. 2: Prognostic value of HA Score in multiple myeloma.

Patients of HM cohort were ranked according to increased HA Score and a maximum difference in OS was obtained with HA Score=−11.3 splitting patients in a high risk (42.7%) and low risk (57.3%) groups. The prognostic value of HA Score was tested on an independent cohort of 345 patients from UAMS treated with TT2 therapy (UAMS-TT2 cohort). The parameters to compute the HA Score of patients of UAMS-TT2 cohort and the proportions delineating the 2 prognostic groups were those defined with HM cohort.

Figure 3:
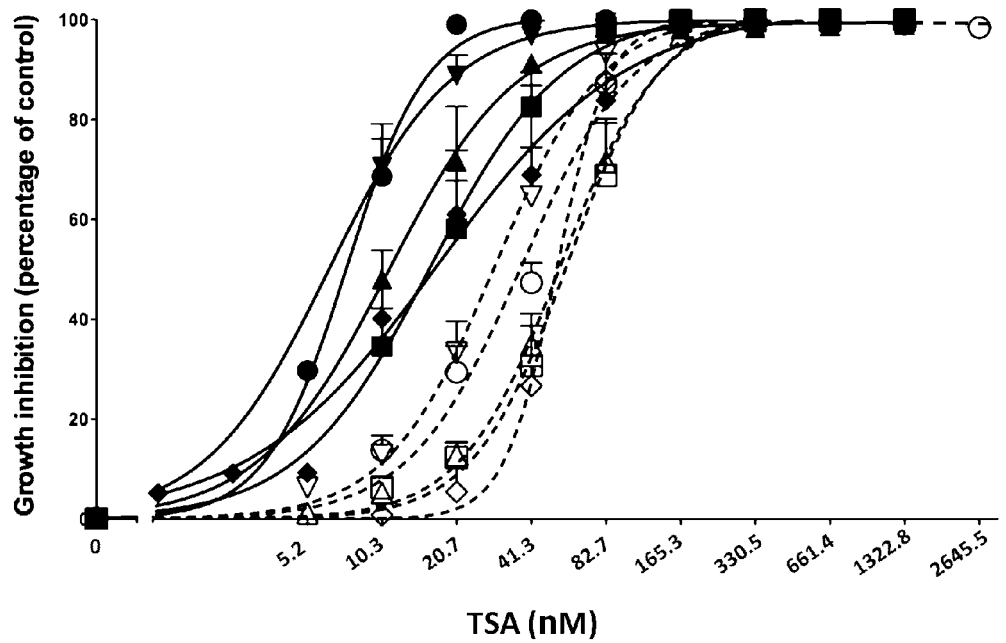

FIG. 3: HA Score predicts for sensitivity of human myeloma cell lines to trichostatin A.

(A) HMCLs with high HA Score (N=5) exhibit significant higher HDACi sensitivity compared to HMCLs with low HA Score (N=5). HMCLs were cultured for 4 days in 96-well flat-bottom microtiter plates in RPMI 1640 medium, 10% FCS, 2 ng/ml IL-6 culture medium (control), with graded TSA concentrations. Data are mean values plus or minus standard deviation (SD) of 5 experiments determined on sextuplet culture wells.

Figure 4:
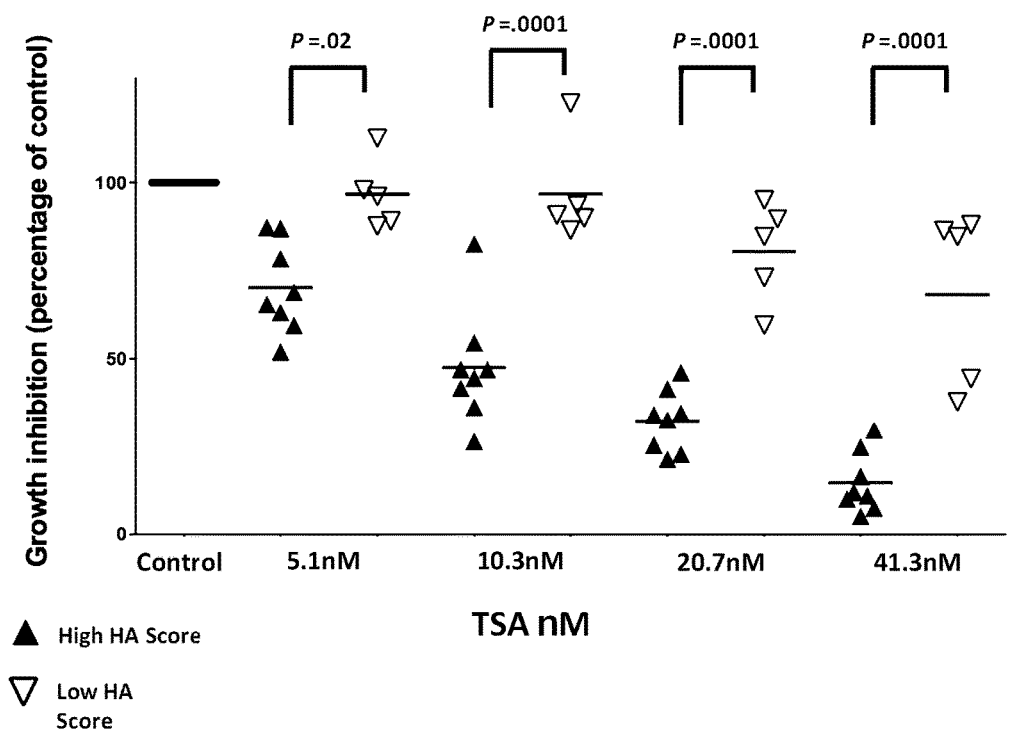

FIG. 4: HA Score predicts for trichostatin A sensitivity of primary myeloma cells of patients. Mononuclear cells from tumor samples of 13 patients with MM were cultured for 4 days in the presence of IL-6 (2 ng/ml) with or without graded TSA concentrations. At day 4 of culture, the cell count and the viability were determined and the percentage of CD138$^+$ viable plasma cells was determined by flow cytometry. Black color represents patients with high HA Score (N=8) and white represents patients with low HA Score values (N=5).

Figure 5A:
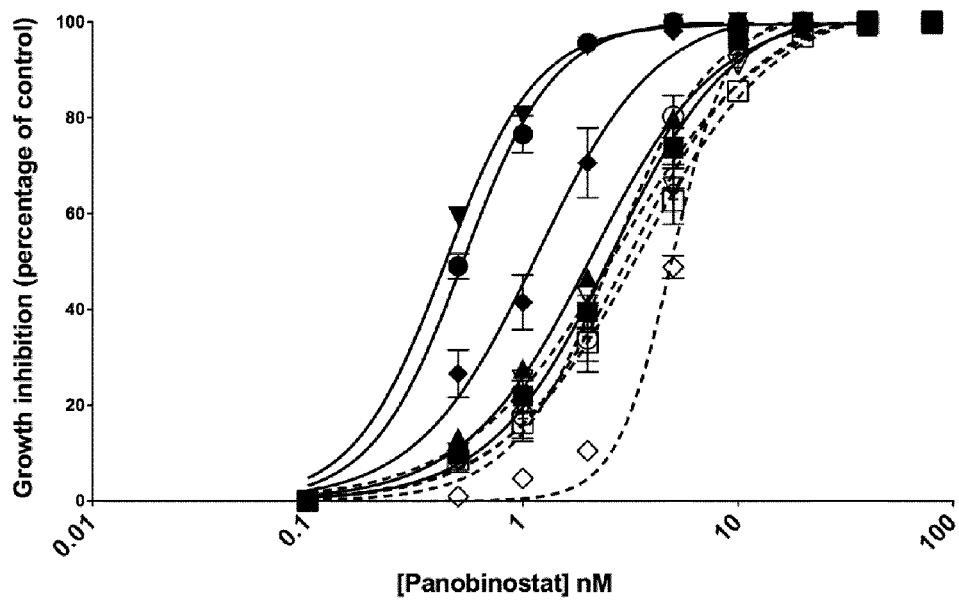
Figure 5B:
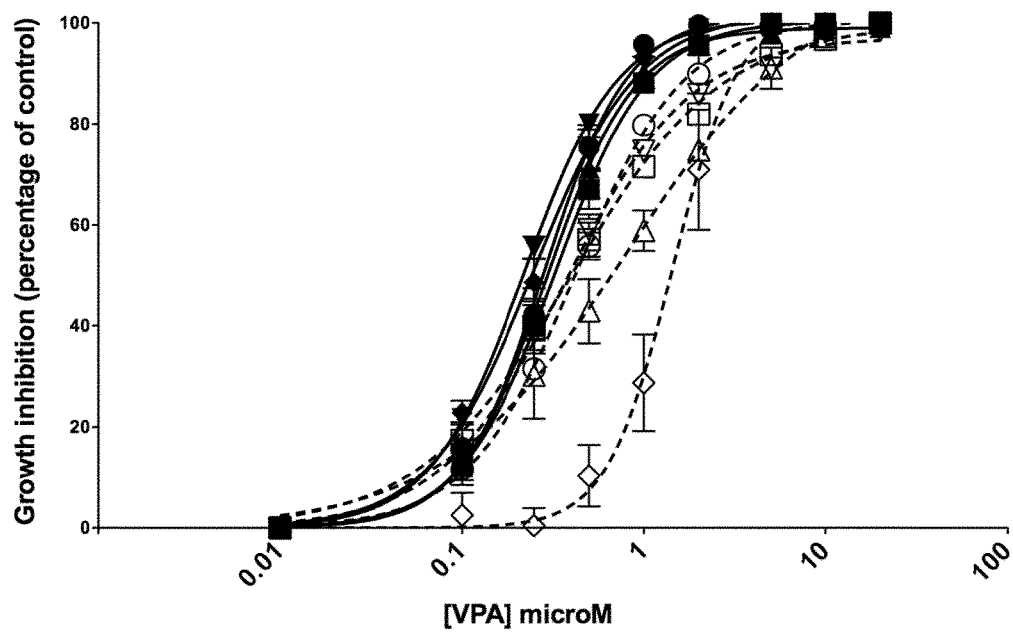
Figure 5C:
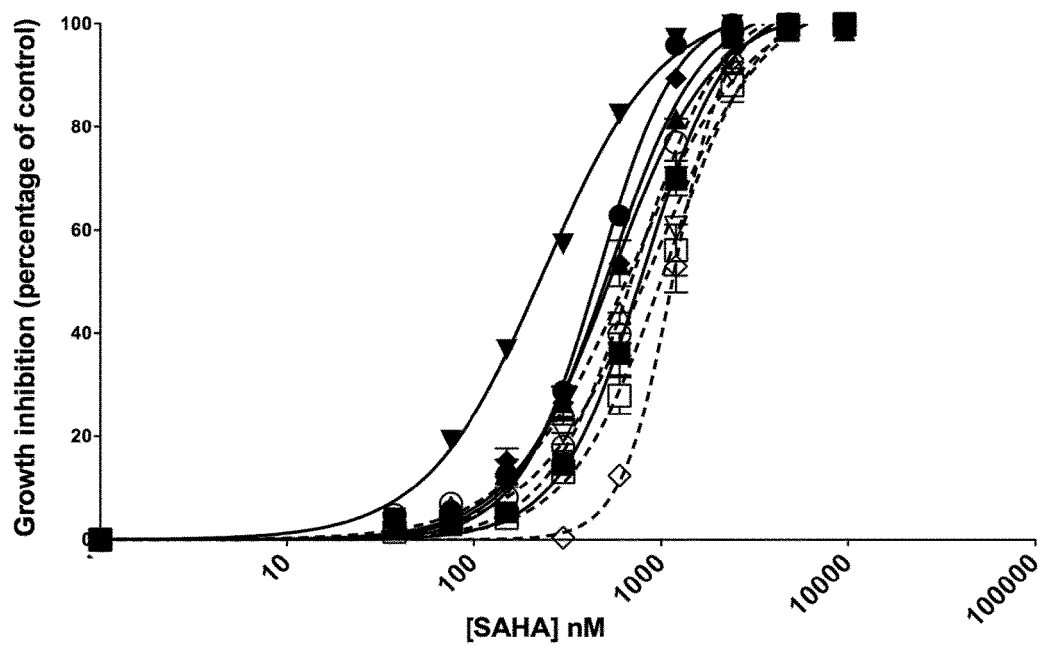

FIG. 5: HA Score predicts for sensitivity of human myeloma cell lines to HDACi in clinical development in MM.

HMCLs with high HA Score (N=5) exhibit significant higher HDACi sensitivity compared to HMCLs with low HA Score (N=5). HMCLs were cultured for 4 days in 96-well flat-bottom microtiter plates in RPMI 1640 medium, 10% FCS, 2 ng/ml IL-6 culture medium (control), with graded Panobinostat (A), VPA (VPA) or SAHA (C) concentrations. Data are mean values plus or minus standard deviation (SD) of 5 experiments determined on sextuplet culture wells.

EXAMPLES

Example 1: Gene Expression-Based Prediction of Myeloma Cell Sensitivity to Histone Deacetylase Inhibitors (Moreaux et al., BJC, 2013)

Material & Methods
Human Myeloma Cell Lines (HMCLs)

XG-1, XG-2, XG-3, XG-4, XG-5, XG-6, XG-7, XG-10, XG-11, XG-12, XG-13, XG-14, XG-16, XG-19, XG-20, XG-21, XG-22, XG-23 and XG-24 human myeloma cell lines were obtained as previously described (25-29). JJN3 was kindly provided by Dr Van Riet (Bruxelles, Belgium), JIM3 by Dr MacLennan (Birmingham, UK) and MM1S by Dr Rosen (Chicago, USA). AMO-1, LP1, L363, U266, OPM2, and SKMM2 were from DSMZ (Germany) and RPMI8226 from ATTC (USA). All HMCLs derived in our laboratory were cultured in the presence of recombinant IL-6. HMCLs microarray data have been deposited in the ArrayExpress public database under accession numbers E-TABM-937 and E-TABM-1088.

Primary Multiple Myeloma Cells

MMCs were purified from 206 patients with newly-diagnosed MM after written informed consent was given at the University hospitals of Heidelberg (Germany) or Montpellier (France). The study was approved by the ethics boards of Heidelberg and Montpellier Universities. These 206 patients were treated with high dose Melphalan (HDM) and autologous stem cell transplantation (ASCT) (30) and were termed in the following Heidelberg-Montpellier (HM) series (Supplementary Table S1). The .CEL files and MASS files have been deposited in the ArrayExpress public database (E-MTAB-372). The inventors also used Affymetrix data of a cohort of 345 purified MMC from previously untreated patients from the University of Arkansas for Medical Sciences (UAMS, Little Rock, Ark.). The patients were treated with total therapy 2 including HDM and ASCT (31) and termed in the following UAMS-TT2 series. These data are publicly available via the online Gene Expression Omnibus (Gene Expression Profile of Multiple Myeloma, accession number GSE2658. http://www.ncbi.nlm.nih.gov/geo/). After ficoll-density gradient centrifugation, plasma cells were purified using anti-CD138 MACS microbeads (Miltenyi Biotech, Bergisch Gladbach, Germany). The t(4; 14) translocation results in aberrant FGFR3 expression in 70% of patients and MMSET spiked expression in 100% of patients (32), and spiked MMSET expression has been taken as surrogate for the presence of t(4; 14) as previously described (33, 34).

Cell Culture and Treatment for Gene Expression Profiling

The human MM cell lines XG-5, XG-6, XG-7, XG-20 and LP1 were grown in RPMI 1640 supplemented with 10% fetal bovine serum and 2 ng/mL recombinant IL-6. Cells ($2\times10^5$/mL) were treated with 0.33 µmol/L TSA (Sigma, St Louis, Mo.) for 24 h. Control cells were cultured in the same conditions without TSA.

Growth Assay for Myeloma Cells

HMCLs were cultured for 4 days in 96-well flat-bottom microtiter plates in RPMI 1640 medium, 10% FCS, 2 ng/ml IL-6 culture medium (control), with graded TSA concentrations. Cell growth was evaluated by quantifying intracellular ATP amount with a Cell Titer Glo Luminescent Assay (Promega, Madison, Wis.) with a Centro LB 960 luminometer (Berthold Technologies, Bad Wildbad, Germany).

Mononuclear Cell Culture

Mononuclear cells from tumor samples of 13 patients with MM were cultured for 4 days at $2\times10^5$ cells/ml in RPMI 1640 medium, 10% FCS, 2 ng/ml IL-6, with or without graded concentrations of TSA, valproic acid (VPA), vorinostat (SAHA) or panobinostat (LBH-589). In each culture group, viability and cell counts were assayed and MMCs were stained with an anti-CD138-PE mAb (Immunotech, Marseille, France) as previously described (35).

Preparation of Complementary RNA (cRNA) and Microarray Hybridization

RNA was extracted using the RNeasy Kit (Qiagen, Hilden, Germany) as previously described (36-37). Biotinylated cRNA was amplified with a double in vitro transcription and hybridized to the human U133 2.0 plus GeneChips, according to the manufacturer's instructions (Affymetrix, Santa Clara, Calif.). Fluorescence intensities were quantified and analyzed using the GECOS software (Affymetrix).

Gene Expression Profiling and Statistical Analyses

Gene expression data were normalized with the MASS algorithm and analyzed with our bioinformatics platforms—RAGE (http://rage.montp.inserm.fr/) (38) and Amazonia (http://amazonia.montp.inserm.fr/) (39)—or SAM (Significance Analysis of Microarrays) software (40). Hierarchical clustering was performed with the Cluster and Treeview softwares from Eisen (41). The event free or overall survival of subgroups of patients was compared with the log-rank test and survival curves computed with the Kaplan-Meier method. The prognostic values of parameters were compared with univariate or multivariate Cox analysis. Statistical comparisons were done with Mann-Whitney, Chi-square, or Student t-tests. Statistical tests were performed with the software package SPSS 12.0 (SPSS, Chicago, Ill.). Biological pathways were analyzed with Ingenuity Pathways Analysis (Ingenuity® Systems, www.ingenuity.com).

Results

Identification of Prognostic Genes Whose Expression is Upregulated by Trichostatin A Treatment of Multiple Myeloma Cells.

Five HMCLs were treated with 0.33 µM TSA for 24 h, a concentration which did not affect myeloma cell viability (Supplementary Table S2) (42). Using SAM supervised paired analysis, the expression of 95 genes was found to be significantly upregulated by TSA treatment of these 5 HMCLs (FDR<5%; Supplementary Table S3). TSA-regulated genes are significantly enriched in genes related to "Immunological disease and Inflammatory disease" pathway (P<0.05; Ingenuity pathway analysis). Looking for the expression of these 95 TSA-regulated genes in primary MMCs of a cohort of 206 newly-diagnosed patients (HM cohort), 16 genes had a bad prognostic value and 21 a good one after Benjamini Hochberg multiple testing correction (Supplementary Table S4). The prognostic information of HDACi regulated genes was gathered within an histone acetylation score (HA Score), which was the sum of the beta coefficients of the Cox model weighted by ±1 according to the patient MMC signal above or below the probe set maxstat value as described (34). The value of HA Score in healthy, premalignant or malignant plasma cells is displayed in FIG. 1. Cells from MGUS patients had a significant higher HA Score than normal BMPCs (P<0.001), MMCs of patients a significantly higher HA Score than normal BMPCs or plasma cells from MGUS-patients (P<0.001), and HMCLs the highest score (P<0.001) (FIG. 1).

Prognostic Value of HA Score Compared to Usual Prognostic Factors.

HA Score had prognostic value when used as a continuous variable ($P \leq 10^{-4}$), or by splitting patients into two groups using Maxstat R function (34). A maximum difference in overall survival (OS) was obtained with HA Score=−11.3 splitting patients in a high-risk group of 42.7% patients (HA Score>−11.3) with a 43.5 months median OS and a low risk group of 57.3% patients (HA Score≤−11.3) with not reached median survival (FIG. 2). Using univariate Cox analysis, HA Score, UAMS-HRS, IFM-score and GPI had prognostic value as well as t(4; 14), del17p, β2m, albumin and ISS using the HM patient cohort (Supplementary Table S5). When compared two by two, HA Score tested with β2m and t(4; 14) remained significant. When these parameters were tested together, HA Score, β2m, t(4; 14) and GPI kept prognostic value. The HA Score is also prognostic in an independent cohort of 345 patients from UAMS treated with TT2 therapy (UAMS-TT2 cohort). For each patient of UAMS-TT2 cohort, HA Score was computed using parameters defined with HM patients' cohort. The median OS of patients within high score group was 71.4 months and not reached for patients with low HA Score (P<0.0001) (FIG. 2). Using Cox univariate analysis, UAMS-HRS, IFM and GPI scores as well as t(4; 14) and del17p had prognostic value. Comparing these prognostic factors two by two, HA Score remained significant compared to UAMS-HRS, IFM, GPI, t(4; 14), and del17p in the UAMS-TT2 cohort (Supplementary Table S5). When these parameters were tested together, HA Score, UAMS-HRS, t(4; 14) and del17p kept prognostic value in UAMS-TT2 cohort.

HA Score is Predictive for Sensitivity of Human Myeloma Cell Lines or Patients' Primary MMCs to Trichostatin A In Vitro.

The inventors sought to determine whether HA Score could predict for the sensitivity of 10 HMCLs to HDAC inhibitor. Starting from a large cohort of 40 HMCLs (25), the 10 HMCLs with the highest or lowest HA Score were selected to assay TSA sensitivity. The 5 HMCLs with the highest HA Score exhibited a significant 5-fold higher TSA sensitivity (median IC50=10.97 nM; range: 6.32 to 17.4 nM) than the 5 HMCLs with low HA Score (P=0.0004; median IC50=52.33 nM; range: 29.49 to 57.74 nM) (FIG. 3). No difference in recurrent genetic abnormalities were found between HMCLs with the highest or lowest HA Score (Table 1).

HA Score is Predictive for Sensitivity of Human Myeloma Cells to Other Clinical Grade HDACi In Vitro The inventors sought to determine whether HA Score could predict for the sensitivity of myeloma cells to clinical grade HDAC inhibitors {Neri, 2012 #3317}. The 5 HMCLs with the highest HA Score exhibited a significant higher Panobinostat, VPA and Vorinostat sensitivity (median IC50=1.16 nM, 0.28 µM and 528 nM respectively) than the 5 HMCLs with low HA score (P=0.007, P=0.009 and P=0.02; median IC50=3.16 nM, 0.43 µM and 897 nM respectively) (FIGS. 5A-B&C).

Discussion

In this study, the inventors have identified a gene expression-based histone acetylation score (HA Score) which is predictive for patients' survival and for the in vitro sensitivity of human myeloma cell lines or patients' primary myeloma cells to a pan-HDAC inhibitor, trichostatin A. Several trials have looked for the efficacy of various HDACi in patients with MM, when used alone (10,21,22) or in combination with usual anti-MMC drugs such as Dexamethasone, Lenalidomide or Bortezomib (10,23,24). These trials indicate a partial response, which could be explained by patients' heterogeneity. The current identification of HA Score should be very useful to investigate whether the higher response to HDACi is found in patients with highest HA Score and to speed up the investigation of the clinical efficacy of the novel agents.

Besides the tility of the current HA Score in selecting patients who could benefit from HDACi therapies, the current study highlights pathways which could be involved in the emergence of multiple myeloma cells. Among the genes upregulated by TSA treatment and associated with a favorable prognosis, the inventors identified NFKBIZ (nuclear factor of kappa light polypeptide gene enhancer in B-cell inhibitor zeta), BASP1 (Brain acid-soluble protein 1) and QKI (Quaking). NFKBIZ is a member of IκB family (43). NFKBIZ protein is localized in the nucleus where it interacts with and regulates nuclear NF-κB activity. Suppression of endogenous NFKBIZ renders cells more resistant to apoptosis, whereas its overexpression induces cell death (43,44). More recently, it was demonstrated that NFKBIZ inhibits the transcriptional activity of STAT3 leading to cell growth inhibition and apoptosis induction mediated by down-regulation of a known STAT3 target, Mcl-1 (45). This is of interest because the inventors previously demonstrated that Mcl-1 is the major antiapoptotic protein involved in IL-6-mediated survival of MMCs (46). BASP1 is a Myc oncogene target that is specifically repressed in Myc-transformed cells and conversely, has a strong potential to inhibit cell transformation induced by Myc (47). The inhibition of Myc induced fibroblast cell transformation by BASP1 also prevents the transcriptional activation or repression of known Myc target genes. BASP1 appears to be a potential tumor suppressor in cancer (47). In MM, malignant features includes activation of Myc and of NF-κB pathway (11,48,49). HDAC inhibitors appear useful to target NF-κB and Myc activation in MMC through upregulation of NFK-BIBZ and BASP1 expression. RNA binding protein QKI belongs to the evolutionarily conserved signal transduction and activator of RNA family. It has been demonstrated that overexpression of QKI induced the G1 cell cycle arrest in oligodendrocyte progenitor cells (50). Furthermore, QKI inhibits colon cancer cell growth, acting as a tumor suppressor (51). It was demonstrated that QKI protein is directly transcribed by E2F1, which in turn negatively regulates the cell cycle by targeting multiple cell cycle regulators including p27, cyclin D1 and c-fos (52). These results demonstrated that a better understanding of the cellular response to epigenetic-targeted treatments will increase our knowledge of MM development and progression and will provide potential therapeutic advances. Epigenetic therapies could be combined with conventional therapies to develop personalized treatments in MM and render resistant tumors responsive to treatment. These advances may limit the side effects of treatment, improving compliance with dosing regimens and overall quality of life. Our methodology could be extended to other anti-MM treatments.

Primary MMCs were cultured with their BM environment and recombinant IL-6 and graded concentrations of TSA for 4 days. Primary MMCs of patients with a HA Score above median value (−11.3, FIG. 1) exhibited significant (P<0.05) 2.4-fold higher TSA sensitivity than MMCs with HA Score below median (FIG. 4 and Table 2). The characteristics of patients with MM included in this study are described in Table 3.

TABLE 2

Mononuclear cells from tumor samples of 12 patients with MM were cultured for 4 days in the presence of IL-6 (2 ng/mL) with or without increased doses of TSA. At day 4 of culture, the cell count and viability were determined and the percentage of CD138+ viable plasma cells was determined by flow cytometry.

| | Patient no. | Myeloma cell number/culture well | | | | |
|---|---|---|---|---|---|---|
| | | Control | 5.1 nM TSA | 10.3 nM TSA | 20.7 nM TSA | 41.3 nM TSA |
| Patients with high HA Score | 1 | 66154 | 43320 | 31086 | 22880 | 7250 |
| | 2 | 114266 | 115520 | 45216 | 20592 | 29000 |
| | 3 | 114266 | 72200 | 50868 | 38896 | 18850 |
| | 4 | 96224 | 83752 | 25434 | 20592 | 11600 |
| | 5 | 33540 | 19950 | 12170 | 7650 | 1736 |
| | 6 | 72168 | 37544 | 33912 | 18304 | 7250 |
| | 7 | 70092 | 48249 | 38249 | 29064 | 5238 |
| | 8 | 100440 | 78844 | 41860 | 32752 | 29790 |
| | Mean | 83394 | 62422 | 34849 | 23841 | 13839 |
| Patients with low HA Score | 1 | 75175 | 72200 | 64998 | 54912 | 33350 |
| | 2 | 69161 | 60648 | 62172 | 41184 | 26100 |
| | 3 | 15072 | 14750 | 18486 | 14328 | 12765 |
| | 4 | 272272 | 306768 | 254478 | 243978 | 235040 |
| | 5 | 21450 | 19100 | 19458 | 18168 | 18876 |
| | Mean | 90626 | 94693 | 83918 | 74514 | 65226 |

TABLE 3

Characteristics of patients with a HA Score above (N = 8) and under (N = 5) the median value.

| | Age | Sex | Monoclonal protein | Durie and Salmon stage | ISS stage | Serum β2-microglobulin | Multiple myeloma molecular classification |
|---|---|---|---|---|---|---|---|
| Patients with high HA Score | | | | | | | |
| Patient 1 | 69 | F | IgG Kappa | IIIA | I | 2.8 | CD2 |

TABLE 1

Characteristics of HMCLs$^{TSA\ sensitive}$ and HMCLs$^{TSA\ resistant}$

| HMCL Name | IL-6 dependence[1] | Origin[2] | Disease[3] | Patient sample[4] | Gender | Isotype | t(14q32 or 22q11;) | Target genes | Ras | TP53 | CD45 | HMCL classification |
|---|---|---|---|---|---|---|---|---|---|---|---|---|
| TSA Resistant HMCLs | | | | | | | | | | | | |
| XG7 | + | MN | MM | PB | F | Ak | t(4; 14) | MMSET | mut | wt | +/− | MS |
| XG20 | ++ | MN | PCL | PB | M | I | t(4; 14) | MMSET | wt | abn | − | MS |
| AMO1 | − | CO | PCT | AF | F | Ak | t(12; 14) | unknown | wt | wt | + | CD-2L |
| JJN3 | − | CO | MM | PE | F | Ak | t(14; 16) | c-Maf | mut | abn | +/− | MF |
| LP1 | − | CO | MM | PB | F | Gl | t(4; 14) | MMSET/FGFR3 | wt | abn | − | MS |
| TSA Sensitive HMCLs | | | | | | | | | | | | |
| XG5 | ++ | MN | MM | PB | F | I | t(11; 14) | CCND1 | wt | abn | − | CD-1 |
| XG6 | ++ | MN | MM | PB | F | Gl | t(16; 22) | c-Maf | wt | wt | + | CTA/MF |
| XG13 | ++ | MN | PCL | PB | M | Gl | t(14; 16) | c-Maf | wt | abn | + | MF |
| XG16 | ++ | MN | PCL | PB | M | k | none | none | mut | abn | + | CTA/FRZB |
| XG21 | ++ | MN | MM | PE | M | I | t(11; 14) | CCND1 | wt | wt | + | CD-1 |

TABLE 3-continued

Characteristics of patients with a HA Score above (N = 8) and under (N = 5) the median value.

| | Age | Sex | Monoclonal protein | Durie and Salmon stage | ISS stage | Serum β2-microglobulin | Multiple myeloma molecular classification |
|---|---|---|---|---|---|---|---|
| Patient 2 | 48 | M | Lambda | NA | NA | NA | CD1 |
| Patient 3 | 55 | M | BJ Kappa | IIIB | III | 10 | HY |
| Patient 4 | 69 | M | IgG Lambda | IIIA | III | 10.4 | PR |
| Patient 5 | 70 | F | IgA Lambda | IIIA | II | 5 | CD2 |
| Patient 6 | 63 | F | Asecret | III | III | 13.5 | CD1 |
| Patient 7 | 54 | M | IgA Lambda | IIIA | I | 2.3 | CD2 |
| Patient 8 | 72 | M | IgG Lambda | IIIA | III | 8.6 | PR |
| Patients with low HA Score | | | | | | | |
| Patient 1 | 63 | M | BJ Lambda | NA | NA | NA | PR |
| Patient 2 | 62 | M | IgA Kappa | IIA | I | 2.6 | HP |
| Patient 3 | 83 | M | IgG Kappa | IIIA | III | 8.3 | HY |
| Patient 4 | 59 | F | IgA Lambda | IIIA | III | 6.7 | MF |
| Patient 5 | 47 | M | IgA Kappa | IIIB | III | 24.4 | PR |

SUPPLEMENTARY TABLE S1

Clinical patient data for age, serum-β2-microglobulin, and plasma cell infiltration in the Heidelberg/Montpellier-group (HM) and the Arkansas cohort. Median value and range are given.

| Characteristic | HM cohort (n = 206) | Arkansas cohort (n = 345) |
|---|---|---|
| Age | 58.5 [27-73] | 57 [25-77] |
| Monoclonal protein | | |
| IgG | 120 | 193 |
| IgA | 46 | 93 |
| Bence Jones | 35 | 47 |
| Asecretory | 4 | 6 |
| IgD | 1 | 3 |
| NA | 0 | 3 |
| Myeloma in Durie and Salmon stage | | |
| I | 22 | NA |
| II | 31 | NA |
| III | 153 | NA |
| Myeloma in ISS stage | | |
| I | 97 | 189 |
| II | 73 | 86 |
| III | 33 | 70 |
| NA | 3 | 0 |
| Serum-β2-microglobulin | 2.99 [1.3-53.6] | 2.9 [1.0-38.7] |
| Plasma cells in bone marrow | 42 [1-100] | 42 [4-98] |

NA, not available.
ISS, International Staging System.

SUPPLEMENTARY TABLE S2

Cell viability of HMCLs treated with 0.33 μM TSA for 24 h. Date are the mean percentages ± SD of viable cells evaluated by trypan blue exclusion (3 experiments).

| | Cell viability (%) | | |
|---|---|---|---|
| | | Day 1 | |
| HMCLS | Day 0 | Control | TSA |
| XG-5 | 70 ± 2 | 70 ± 2 | 70 ± 3 |
| XG-6 | 100 ± 0 | 100 ± 0 | 100 ± 1 |
| XG-7 | 100 ± 0 | 100 ± 0 | 100 ± 0 |
| XG-20 | 100 ± 0 | 100 ± 0 | 100 ± 1 |
| LP1 | 100 ± 0 | 100 ± 0 | 100 ± 0 |

SUPPLEMENTARY TABLE S3

Genes overexpressed in TSA treated HMCLs. Five HMCLs were cultured with or without 0.33 μM TSA for 1 day and gene expression was profiled with Affymetrix U133 plus 2.0. Genes significantly differentially expressed between control and TSA treated cells were identified using SAM supervised paired analysis with a 5% false discovery rate. When a gene was interrogated by several probe sets, we used the probe set yielding to a maximum variance across control and TSA treated cells.

| Probeset | Gene | Ratio | Banding | Affymetrix description |
|---|---|---|---|---|
| Intercellular communication and membrane proteins | | | | |
| 209462_at | APLP1 | 3.37 | 19q13.1 | amyloid beta (A4) precursor-like protein 1 |
| 214875_x_at | APLP2 | 1.62 | 11q23-q25\|11q24 | amyloid beta (A4) precursor-like protein 2 |
| 209906_at | C3AR1 | 7.86 | 12p13.31 | complement component 3a receptor 1 |
| 1557905_s_at | CD44 | 2.69 | 11p13 | CD44 antigen (homing function and Indian blood group system) |
| 219505_at | CECR1 | 1.86 | 22q11.2 | cat eye syndrome chromosome region; candidate 1 |
| 215388_s_at | CFH | 1.94 | 1q32 | complement factor H |
| 209732_at | CLEC2B | 1.84 | 12p13-p12 | C-type lectin domain family 2; member B |

SUPPLEMENTARY TABLE S3-continued

Genes overexpressed in TSA treated HMCLs. Five HMCLs were cultured with or without 0.33 μM TSA for 1 day and gene expression was profiled with Affymetrix U133 plus 2.0. Genes significantly differentially expressed between control and TSA treated cells were identified using SAM supervised paired analysis with a 5% false discovery rate. When a gene was interrogated by several probe sets, we used the probe set yielding to a maximum variance across control and TSA treated cells.

| Probeset | Gene | Ratio | Banding | Affymetrix description |
|---|---|---|---|---|
| 226281_at | DNER | 15.70 | 2q36.3 | delta-notch-like EGF repeat-containing transmembrane |
| 212464_s_at | FN1 | 5.28 | 2q34 | fibronectin 1 |
| 216041_x_at | GRN | 2.58 | 17q21.32 | granulin |
| 200696_s_at | GSN | 5.81 | 9q33 | gelsolin (amyloidosis; Finnish type) |
| 211990_at | HLA-DPA1 | 2.02 | 6p21.3 | major histocompatibility complex; class II; DP alpha 1 |
| 201137_s_at | HLA-DPB1 | 1.51 | 6p21.3 | major histocompatibility complex; class II; DP beta 1 |
| 212998_x_at | HLA-DQB1 | 1.51 | 6p21.3 | major histocompatibility complex; class II; DQ beta 1 |
| 208894_at | HLA-DRA | 1.58 | 6p21.3 | major histocompatibility complex; class II; DR alpha |
| 215193_x_at | HLA-DRB1 | 1.64 | 6p21.3 | major histocompatibility complex; class II; DR beta 1 |
| 216331_at | ITGA7 | 2.18 | 12q13 | integrin; alpha 7 |
| 214020_x_at | ITGB5 | 2.73 | 3q21.2 | Integrin; beta 5 |
| 203413_at | NELL2 | 6.16 | 12q13.11-q13.12 | NEL-like 2 (chicken) |
| 204563_at | SELL | 4.02 | 1q23-q25 | selectin L (lymphocyte adhesion molecule 1) |
| 228726_at | SERPINB1 | 2.97 | 6p25 | Serpin peptidase inhibitor; clade B (ovalbumin); member 1 |
| 205352_at | SERPINI1 | 4.22 | 3q26.1 | serpin peptidase inhibitor; clade I (neuroserpin); member 1 |
| 209848_s_at | SILV | 26.38 | 12q13-q14 | silver homolog (mouse) |
| 1569003_at | TMEM49 | 2.57 | 17q23.2 | transmembrane protein 49 |
| Signal transduction | | | | |
| 221718_s_at | AKAP13 | 2.18 | 15q24-q25 | A kinase (PRKA) anchor protein 13 |
| 218501_at | ARHGEF3 | 2.01 | 3p21-p13 | Rho guanine nucleotide exchange factor (GEF) 3 |
| 219546_at | BMP2K | 2.43 | 4q21.21 | BMP2 inducible kinase |
| 208891_at | DUSP6 | 1.99 | 12q22-q23 | dual specificity phosphatase 6 |
| 226269_at | GDAP1 | 1.91 | 8q21.11 | Ganglioside-induced differentiation-associated protein 1 |
| 223218_s_at | NFKBIZ | 2.70 | 3p12-q12 | nuclear factor of kappa light polypeptide gene enhancer in B-cells inhibitor; zeta |
| 203355_s_at | PSD3 | 4.19 | 8pter-p23.3 | pleckstrin and Sec7 domain containing 3 |
| 204944_at | PTPRG | 1.80 | 3p21-p14 | protein tyrosine phosphatase; receptor type; G |
| 230233_at | RASGEF1B | 4.44 | 4q21.3 | RasGEF domain family; member 1B |
| 226436_at | RASSF4 | 1.32 | 10q11.21 | Ras association (RalGDS/AF-6) domain family 4 |
| 216834_at | RGS1 | 2.68 | 1q31 | regulator of G-protein signalling 1 |
| 34408_at | RTN2 | 3.75 | 19q13.32 | reticulon 2 |
| 209969_s_at | STAT1 | 3.72 | 2q32.2 | signal transducer and activator of transcription 1; 91 kDa |
| Cytoskeleton | | | | |
| 200965_s_at | ABLIM1 | 1.98 | 10q25 | actin binding LIM protein 1 |
| 206385_s_at | ANK3 | 2.57 | 10q21 | ankyrin 3; node of Ranvier (ankyrin G) |
| 225481_at | FRMD6 | 1.23 | 14q22.1 | FERM domain containing 6 |
| 203854_at | IF | 3.96 | 4q25 | I factor (complement) |
| 224823_at | MYLK | 1.71 | 3q21 | myosin; light polypeptide kinase |
| 218678_at | NES | 1.50 | 1q23.1 | nestin |
| 209958_s_at | PTHB1 | 2.03 | 7p14 | parathyroid hormone-responsive B1 |
| Cell cycle | | | | |
| 209304_x_at | GADD45B | 1.51 | 19p13.3 | growth arrest and DNA-damage-inducible; beta |
| Metabolism | | | | |
| 213106_at | ATP8A1 | 2.60 | 4p14-p12 | ATPase; aminophospholipid transporter (APLT); Class I; type 8A; member 1 |
| 213317_at | CLIC5 | 4.98 | 6p12.1-21.1 | Chloride intracellular channel 5 |

SUPPLEMENTARY TABLE S3-continued

Genes overexpressed in TSA treated HMCLs. Five HMCLs were cultured with or without 0.33 μM TSA for 1 day and gene expression was profiled with Affymetrix U133 plus 2.0. Genes significantly differentially expressed between control and TSA treated cells were identified using SAM supervised paired analysis with a 5% false discovery rate. When a gene was interrogated by several probe sets, we used the probe set yielding to a maximum variance across control and TSA treated cells.

| Probeset | Gene | Ratio | Banding | Affymetrix description |
|---|---|---|---|---|
| 214079_at | DHRS2 | 8.51 | 14q11.2 | dehydrogenase/reductase (SDR family) member 2 |
| 201431_s_at | DPYSL3 | 2.55 | 5q32 | dihydropyrimidinase-like 3 |
| 219833_s_at | EFHC1 | 3.22 | 6p12.3 | EF-hand domain (C-terminal) containing 1 |
| 210299_s_at | FHL1 | 1.34 | Xq26 | four and a half LIM domains 1 |
| 202838_at | FUCA1 | 3.52 | 1p34 | fucosidase; alpha-L-1; tissue |
| 218918_at | MAN1C1 | 2.10 | 1p35 | mannosidase; alpha; class 1C; member 1 |
| 211685_s_at | NCALD | 1.80 | 8q22-q23 | neurocalcin delta |
| 201468_s_at | NQO1 | 2.29 | 16q22.1 | NAD(P)H dehydrogenase; quinone 1 |
| 1555426_a_at | OTUD5 | 2.50 | Xp11.23 | OTU domain containing 5 |
| 207808_s_at | PROS1 | 3.03 | 3q11.2 | protein S (alpha) |
| 210432_s_at | SCN3A | 1.37 | 2q24 | sodium channel; voltage-gated; type III; alpha |
| 224818_at | SORT1 | 1.97 | 1p21.3-p13.1\|1p21.3-p13.1 | sortilin 1 |
| 206310_at | SPINK2 | 7.86 | 4q12 | serine peptidase inhibitor; Kazal type 2 (acrosin-trypsin inhibitor) |
| Protein binding | | | | |
| 202391_at | BASP1 | 1.30 | 5p15.1-p14 | brain abundant; membrane attached signal protein 1 |
| 208791_at | CLU | 2.55 | 8p21-p12 | clusterin (complement lysis inhibitor; SP-40; 40; sulfated glycoprotein 2; testosterone-repressed prostate message 2; apolipoprotein J) |
| 203695_s_at | DFNA5 | 7.46 | 7p15 | deafness; autosomal dominant 5 |
| 226158_at | KLHL24 | 2.32 | 3q27.1 | kelch-like 24 (*Drosophila*) |
| 204745_x_at | MT1G | 2.61 | 16q13 | metallothionein 1G |
| 212185_x_at | MT2A | 2.54 | 16q13 | metallothionein 2A |
| 202073_at | OPTN | 2.93 | 10p13 | optineurin |
| 209198_s_at | SYT11 | 6.99 | 1q21.2 | synaptotagmin XI |
| 213361_at | TDRD7 | 2.36 | 9q22.33 | tudor domain containing 7 |
| 201009_s_at | TXNIP | 2.52 | 1q21.1 | thioredoxin interacting protein |
| Nuclear proteins and transcription factors | | | | |
| 205249_at | EGR2 | 6.47 | 10q21.1 | early growth response 2 (Krox-20 homolog; *Drosophila*) |
| 228260_at | ELAVL2 | 2.97 | 9p21 | ELAV (embryonic lethal; abnormal vision; *Drosophila*)-like 2 (Hu antigen B) |
| 219209_at | IFIH1 | 2.33 | 2p24.3-q24.3 | interferon induced with helicase C domain 1 |
| 238430_x_at | MGC19764 | 3.16 | 17q12 | likely ortholog of mouse schlafen 5 |
| 223484_at | NMES1 | 7.17 | 15q21.1 | normal mucosa of esophagus specific 1 |
| 205552_s_at | OAS1 | 2.79 | 12q24.1 | 2prime; 5prime-oligoadenylate synthetase 1; 40/46 kDa |
| 224701_at | PARP14 | 2.73 | 3q21.1 | poly (ADP-ribose) polymerase family; member 14 |
| 212636_at | QKI | 3.04 | 6q26-27 | quaking homolog; KH domain RNA binding (mouse) |
| 225123_at | SESN3 | 5.02 | 11q21 | Sestrin 3 |
| 222651_s_at | TRPS1 | 2.08 | 8q24.12 | trichorhinophalangeal syndrome I |
| Apoptosis | | | | |
| 201012_at | ANXA1 | 7.51 | 9q12-q21.2\|9q12-q21.2 | annexin A1 |
| 210538_s_at | BIRC3 | 4.09 | 11q22 | baculoviral IAP repeat-containing 3 |
| 226530_at | BMF | 2.19 | 15q14 | Bcl2 modifying factor |
| 204415_at | G1P3 | 2.81 | 1p35 | interferon; alpha-inducible protein (clone IFI-6-16) |
| Others | | | | |
| 236099_at | — | 1.78 | — | Transcribed locus |
| 215079_at | — | 1.45 | — | LOC441207 |
| 226725_at | — | 3.75 | — | Transcribed locus |
| 225842_at | — | 2.10 | — | CDNA clone IMAGE: 5531727 |
| 231040_at | — | 1.78 | — | CDNA FLJ43172 fis; clone FCBBF3007242 |

SUPPLEMENTARY TABLE S3-continued

Genes overexpressed in TSA treated HMCLs. Five HMCLs were cultured with or without 0.33 μM TSA for 1 day and gene expression was profiled with Affymetrix U133 plus 2.0. Genes significantly differentially expressed between control and TSA treated cells were identified using SAM supervised paired analysis with a 5% false discovery rate. When a gene was interrogated by several probe sets, we used the probe set yielding to a maximum variance across control and TSA treated cells.

| Probeset | Gene | Ratio | Banding | Affymetrix description |
| --- | --- | --- | --- | --- |
| 219637_at | ARMC9 | 4.55 | 2q37.1 | armadillo repeat containing 9 |
| 229973_at | C1orf173 | 8.67 | 1p31.1 | chromosome 1 open reading frame 173 |
| 228152_s_at | FLJ31033 | 4.08 | 4q32.3 | hypothetical protein FLJ31033 |
| 235301_at | KIAA1324L | 2.26 | 7q21.12 | KIAA1324-like |
| 225688_s_at | PHLDB2 | 6.58 | 3q13.2 | pleckstrin homology-like domain; family B; member 2 |
| 203567_s_at | TRIM38 | 2.83 | 6p21.3 | tripartite motif-containing 38 |

SUPPLEMENTARY TABLE S4

Prognostic value of TSA deregulated genes in primary MMC of newly-diagnosed patients.

| Probeset | NAME | Ajusted P value (Benjamini hochberg multiple testing correction) | Hazard ratio |
| --- | --- | --- | --- |
| Bad prognostic genes | | | |
| 204563_at | SELL | .04 | 1.94 |
| 203567_s_at | TRIM38 | .04 | 1.96 |
| 201012_at | ANXA1 | .02 | 2.01 |
| 205352_at | SERPINI1 | .04 | 2.03 |
| 204944_at | PTPRG | .01 | 2.12 |
| 222651_s_at | TRPS1 | .03 | 2.17 |
| 214875_x_at | APLP2 | .01 | 2.19 |
| 203854_at | IF | .03 | 2.34 |
| 209958_s_at | PTHB1 | .01 | 2.35 |
| 209969_s_at | STAT1 | .009 | 2.37 |
| 205552_s_at | OAS1 | .01 | 2.50 |
| 226269_at | GDAP1 | .008 | 2.69 |
| 210432_s_at | SCN3A | .007 | 2.71 |
| 224701_at | PARP14 | .01 | 2.94 |
| 214079_at | DHRS2 | 4.76e−05 | 3.11 |
| 226158_at | KLHL24 | .01 | 3.44 |
| Good prognostic genes | | | |
| 34408_at | RTN2 | 2.42e−05 | .28 |
| 225842_at | — | 9.96e−05 | .32 |
| 208894_at | HLA-DRA | .01 | .36 |
| 212464_s_at | FN1 | .01 | .37 |
| 202391_at | BASP1 | 7.01e−05 | .37 |
| 228726_at | SERPINB1 | .009 | .38 |
| 235301_at | KIAA1324L | .01 | .39 |
| 206385_s_at | ANK3 | .007 | .40 |
| 230233_at | RASGEF1B | .04 | .42 |
| 215193_x_at | HLA-DRB1 | .01 | .43 |
| 212636_at | QKI | .02 | .44 |
| 212998_x_at | HLA-DQB1 | .01 | .47 |
| 223218_s_at | NFKBIZ | .03 | .47 |
| 209198_s_at | SYT11 | .03 | .48 |
| 211990_at | HLA-DPA1 | .02 | .49 |
| 218918_at | MAN1C1 | .04 | .49 |
| 215388_s_at | CFH /// CFHL1 | .04 | .52 |
| 228152_s_at | FLJ31033 | .03 | .53 |
| 216834_at | RGS1 | .04 | .54 |
| 203695_s_at | DFNA5 | .04 | .54 |
| 219833_s_at | EFHC1 | .04 | .55 |

SUPPLEMENTARY TABLES S5

Cox univariate and multivariate analysis of OS in HM and TT2 patients' cohorts.

| | Pronostic variable | HM Cohort OAS | | TT2 Cohort OAS | |
| --- | --- | --- | --- | --- | --- |
| | | Proportional hazard ratio | P-value | Proportional hazard ratio | P-value |
| Univariate COX analysis - Overall survival | HA Score | 18.07 | <.0001 | 1.95 | <.0001 |
| | β2m | 1.1 | <.0001 | NA | NA |
| | ISS | 1.73 | .001 | NA | NA |
| | HRS | 2.37 | .01 | 4.67 | <.0001 |
| | IFM score | 3.09 | .0001 | 1.78 | .004 |
| | t(4; 14) | 2.14 | .001 | 2.21 | .001 |
| | del17p | 3.44 | .02 | 2.46 | <.0001 |
| | GPI | 2.21 | .0001 | 1.75 | <.0001 |
| Multivariate COX analysis - Overall survival | HA Score | 15.71 | <.0001 | NA | NA |
| | ISS | 1.44 | NS | NA | NA |
| | HA Score | 16.49 | <.0001 | NA | NA |
| | β2m | 1.1 | .008 | NA | NA |
| | HA Score | 17.39 | <.0001 | 1.57 | .02 |
| | HRS | 1.88 | NS | 4.11 | <.0001 |
| | HA Score | 17.34 | <.0001 | 1.83 | .002 |
| | IFM score | 1.44 | NS | 1.61 | 0.02 |
| | HA Score | 16.70 | <.0001 | 1.91 | .001 |
| | t(4; 14) | 2.38 | .01 | 2.15 | .001 |
| | HA Score | 14.41 | <.0001 | 1.90 | .001 |
| | del17p | 1.63 | NS | 2.37 | .001 |
| | HA Score | 15.56 | <.0001 | 1.68 | .009 |
| | GPI | 1.65 | NS | 1.55 | .005 |
| Multivariate COX analysis - Overall survival | HA Score | 10.85 | <.0001 | 1.50 | .03 |
| | β2m | 1.1 | .02 | NA | NA |
| | ISS | 1.13 | NS | NA | NA |
| | HRS | 1.70 | NS | 3.92 | <.0001 |
| | IFM score | .45 | NS | .89 | NS |
| | t(4; 14) | 3.89 | .003 | 2.32 | .001 |
| | del17p | 1.42 | NS | 2.35 | .001 |
| | GPI | 2.11 | .03 | 1.19 | NS |

The prognostic factors were tested as single variable or multi variables using Cox-model. P-values and the hazard ratios (HR) are shown. NS, Not significant at a 5% threshold; GPI, gene expression based proliferation index; ISS, International Staging System; HRS, high-risk score; IFM, Intergroupe Francophone du Myélome; NA, Not available.

Example 2

In order to identify the minimal number of genes among the 37 genes used to calculate the HA score, the inventors used PAM (Prediction Analysis of Microarray) statistical technique used for class prediction from gene expression data using nearest shrunken centroids. 34 genes were identified and are depicted in Table B.

TABLE B the minimal number of genes among the 37 genes used to calculate the HA score.

| Gene Symbol | Gene name | Gene ID |
|---|---|---|
| SCN3A | sodium channel, voltage-gated, type III, alpha subunit | 210432_s_at |
| ANK3 | ankyrin 3 | 206385_s_at |
| APLP2 | amyloid beta (A4) precursor-like protein 2 | 214875_x_at |
| QKI | quaking homolog, KH domain RNA binding | 212636_at |
| SYT11 | synaptotagmin XI | 209198_s_at |
| KIAA1324L | KIAA1324-like | 235301_at |
| DHRS2 | dehydrogenase/reductase (SDR family) member 2 | 214079_at |
| DFNA5 | deafness, autosomal dominant 5 | 203695_s_at |
| STAT1 | signal transducer and activator of transcription 1 | 209969_s_at |
| SERPINI1 | serpin peptidase inhibitor, clade I (neuroserpin), member 1 | 205352_at |
| BBS9 or PTHB1 | Bardet-Biedl syndrome 9 or parathyroid hormone-responsive B1 | 209958_s_at |
| RGS1 | regulator of G-protein signaling 1 | 216834_at |
| HLA-DPA1 | major histocompatibility complex, class II, DP alpha 1 | 211990_at |
| FN1 | fibronectin 1 | 212464_s_at |
| KLHL24 | kelch-like 24 | 226158_at |
| HLA-DRA | major histocompatibility complex, class II, DR alpha | 208894_at |
| PTPRG | protein tyrosine phosphatase, receptor type, G | 204944_at |
| RASGEF1B | RasGEF domain family; member 1B | 230233_at |
| OAS1 | 2',5'-oligoadenylate synthetase 1 | 205552_s_at |
| TRIM38 | tripartite motif-containing 38 | 203567_s_at |
| SERPINB1 | Serpin peptidase inhibitor; clade B (ovalbumin); member 1 | 228726_at |
| TRPS1 | trichorhinophalangeal syndrome I | 222651_s_at |
| CFHR1 or CFHL1 | complement factor H-related 1 | 215388_s_at |
| PHLDA1 | pleckstrin homology-like domain, family A, member 1 | 225842_at |
| HLA-DQB1 | major histocompatibility complex, class II, DQ beta 1 | 212998_x_at |
| SELL | selectin L | 204563_at |
| HLA-DRB1 | major histocompatibility complex; class II; DR beta 1 | 215193_x_at |
| NFKBIZ | nuclear factor of kappa light polypeptide gene enhancer in B-cells inhibitor, zeta | 223218_s_at |
| PARP14 | poly (ADP-ribose) polymerase family, member 14 | 224701_at |
| CFI | complement factor I | 203854_at |
| MAN1C1 | mannosidase, alpha, class 1C, member 1 | 218918_at |
| BASP1 | brain abundant, membrane attached signal protein 1 | 202391_at |
| GDAP1 | ganglioside-induced differentiation-associated protein 1 | 226269_at |
| EFHC1 | EF-hand domain (C-terminal) containing 1 | 219833_s_at |

REFERENCES

Throughout this application, various references describe the state of the art to which this invention pertains. The disclosures of these references are hereby incorporated by reference into the present disclosure.

1. Hahn W C, Weinberg R A. Rules for making human tumor cells. N Engl J Med. Nov. 14, 2002; 347(20):1593-1603.

2. Vogelstein B, Kinzler K W. Cancer genes and the pathways they control. Nat Med. August 2004; 10(8):789-799.

3. Baylin S B. DNA methylation and gene silencing in cancer. Nat Clin Pract Oncol. December 2005; 2 Suppl 1:S4-11.

4. Kondo Y. Epigenetic cross-talk between DNA methylation and histone modifications in human cancers. Yonsei Med J. Aug. 31, 2009; 50(4):455-463.

5. Issa J P. DNA methylation as a therapeutic target in cancer. Clin Cancer Res. Mar. 15, 2007; 13(6):1634-1637.

6. Issa J P, Garcia-Manero G, Giles F J, et al. Phase 1 study of low-dose prolonged exposure schedules of the hypomethylating agent 5-aza-2'-deoxycytidine (decitabine) in hematopoietic malignancies. Blood. Mar. 1, 2004; 103 (5):1635-1640.

7. Oki Y, Jelinek J, Shen L, Kantarjian H M, Issa J P. Induction of hypomethylation and molecular response after decitabine therapy in patients with chronic myelomonocytic leukemia. Blood. Feb. 15, 2008; 111(4):2382-2384.

8. Smith E M, Boyd K, Davies F E. The potential role of epigenetic therapy in multiple myeloma. Br J Haematol. Nov. 13, 2009.

9. Lane A A, Chabner B A. Histone deacetylase inhibitors in cancer therapy. J Clin Oncol. Nov. 10, 2009; 27(32):5459-5468.

10. Neri P, Bahlis N J, Lonial S. Panobinostat for the treatment of multiple myeloma. Expert Opin Investig Drugs. Mar. 12, 2012.

11. Bergsagel P L, Kuehl W M. Molecular pathogenesis and a consequent classification of multiple myeloma. J Clin Oncol. Sep. 10, 2005; 23(26):6333-6338.

12. Hideshima T, Bergsagel P L, Kuehl W M, Anderson K C. Advances in biology of multiple myeloma: clinical applications. Blood. Aug. 1, 2004; 104(3):607-618.

13. Lavelle D, Chen Y H, Hankewych M, DeSimone J. Histone deacetylase inhibitors increase p21(WAF1) and induce apoptosis of human myeloma cell lines independent of decreased IL-6 receptor expression. Am J Hematol. November 2001; 68(3):170-178.

14. Mitsiades C S, Mitsiades N S, McMullan C J, et al. Transcriptional signature of histone deacetylase inhibition in multiple myeloma: biological and clinical implications. Proc Natl Acad Sci USA. Jan. 13, 2004; 101(2):540-545.

15. Mitsiades N, Mitsiades C S, Richardson P G, et al. Molecular sequelae of histone deacetylase inhibition in human malignant B cells. Blood. 2003; 16:16.

16. Catley L, Weisberg E, Tai Y T, et al. NVP-LAQ824 is a potent novel histone deacetylase inhibitor with significant activity against multiple myeloma. Blood. Oct. 1, 2003; 102(7):2615-2622.

17. Khan S B, Maududi T, Barton K, Ayers J, Alkan S. Analysis of histone deacetylase inhibitor, depsipeptide (FR901228), effect on multiple myeloma. Br J Haematol. April 2004; 125(2):156-161.

18. Feng R, Ma H, Hassig C A, et al. KD5170, a novel mercaptoketone-based histone deacetylase inhibitor, exerts antimyeloma effects by DNA damage and mitochondrial signaling. Mol Cancer Ther. June 2008; 7(6):1494-1505.

19. Kaiser M, Zavrski I, Sterz J, et al. The effects of the histone deacetylase inhibitor valproic acid on cell cycle, growth suppression and apoptosis in multiple myeloma. Haematologica. February 2006; 91(2):248-251.

20. Neri P, Tagliaferri P, Di Martino M T, et al. In vivo anti-myeloma activity and modulation of gene expression profile induced by valproic acid, a histone deacetylase inhibitor. Br J Haematol. November 2008; 143(4):520-531.

21. Richardson P, Mitsiades C, Colson K, et al. Phase I trial of oral vorinostat (suberoylanilide hydroxamic acid, SAHA) in patients with advanced multiple myeloma. Leuk Lymphoma. March 2008; 49(3):502-507.

22. Niesvizky R, Ely S, Mark T, et al. Phase 2 trial of the histone deacetylase inhibitor romidepsin for the treatment of refractory multiple myeloma. Cancer. Jan. 15, 2011; 117(2):336-342.

23. Badros A, Burger A M, Philip S, et al. Phase I study of vorinostat in combination with bortezomib for relapsed and refractory multiple myeloma. Clin Cancer Res. Aug. 15, 2009; 15(16):5250-5257.

24. Harrison S J, Quach H, Link E, et al. A high rate of durable responses with romidepsin, bortezomib, and dexamethasone in relapsed or refractory multiple myeloma. Blood. Dec. 8, 2011; 118(24):6274-6283.

25. Moreaux J, Klein B, Bataille R, et al. A high-risk signature for patients with multiple myeloma established from the molecular classification of human myeloma cell lines. Haematologica. April 2011; 96(4):574-582.

26. Zhang X G, Gaillard J P, Robillard N, et al. Reproducible obtaining of human myeloma cell lines as a model for tumor stem cell study in human multiple myeloma. Blood. 1994; 83(12):3654-3663.

27. Rebouissou C, Wijdenes J, Autissier P, et al. A gp130 interleukin-6 transducer-dependent SCID model of human multiple myeloma. Blood. 1998; 91(12):4727-4737.

28. Tarte K, Zhang X G, Legouffe E, et al. Induced expression of B7-1 on myeloma cells following retroviral gene transfer results in tumor-specific recognition by cytotoxic T cells. J Immunol. 1999; 163(1):514-524.

29. Gu Z J, Vos J D, Rebouissou C, et al. Agonist anti-gp130 transducer monoclonal antibodies are human myeloma cell survival and growth factors. Leukemia. 2000; 14(1):188-197.

30. Goldschmidt H, Sonneveld P, Cremer F W, et al. Joint HOVON-50/GMMG-HD3 randomized trial on the effect of thalidomide as part of a high-dose therapy regimen and as maintenance treatment for newly diagnosed myeloma patients. Ann Hematol. October 2003; 82(10):654-659.

31. Barlogie B, Tricot G, Rasmussen E, et al. Total therapy 2 without thalidomide in comparison with total therapy 1: role of intensified induction and posttransplantation consolidation therapies. Blood. Apr. 1, 2006; 107(7):2633-2638.

32. Santra M, Zhan F, Tian E, Barlogie B, Shaughnessy J, Jr. A subset of multiple myeloma harboring the t(4; 14)(p16; q32) translocation lacks FGFR3 expression but maintains an IGH/MMSET fusion transcript. Blood. Mar. 15, 2003; 101 (6):2374-2376.

33. Sprynski A C, Hose D, Caillot L, et al. The role of IGF-1 as a major growth factor for myeloma cell lines and the prognostic relevance of the expression of its receptor. Blood. May 7, 2009; 113(19):4614-4626.

34. Kassambara A, Hose D, Moreaux J, et al. Genes with a spike expression are clustered in chromosome (sub)bands and spike (sub)bands have a powerful prognostic value in patients with multiple myeloma. Haematologica. Nov. 18, 2011.

35. Moreaux J, Legouffe E, Jourdan E, et al. BAFF and APRIL protect myeloma cells from apoptosis induced by interleukin 6 deprivation and dexamethasone. Blood. Apr. 15, 2004; 103(8):3148-3157.

36. Hose D, Reme T, Meissner T, et al. Inhibition of aurora kinases for tailored risk-adapted treatment of multiple myeloma. Blood. Apr. 30, 2009; 113(18):4331-4340.

37. Moreaux J, Cremer F W, Reme T, et al. The level of TACI gene expression in myeloma cells is associated with a signature of microenvironment dependence versus a plasmablastic signature. Blood. Aug. 1, 2005; 106(3):1021-1030.

38. Reme T, Hose D, De Vos J, et al. A new method for class prediction based on signed-rank algorithms applied to Affymetrix microarray experiments. BMC bioinformatics. 2008; 9:16.

39. Tanguy Le Carrour S A, Sylvie Tondeur, Ludovic Lhermitte, Ned Lamb, Thierry Reme, Veronique Pantesco, Samir Hamamah, Bernard Klein, John De Vos. Amazonia!: An Online Resource to Google and Visualize Public Human whole Genome Expression Data. The Open Bioinformatics Journal. 2010; 4:5-10.

40. Cui X, Churchill G A. Statistical tests for differential expression in cDNA microarray experiments. Genome Biol. 2003; 4(4):210.

41. Eisen M B, Spellman P T, Brown P O, Botstein D. Cluster analysis and display of genome-wide expression patterns. Proc Natl Acad Sci USA. Dec. 8, 1998; 95(25):14863-14868.

42. Heller G, Schmidt W M, Ziegler B, et al. Genome-wide transcriptional response to 5-aza-2'-deoxycytidine and trichostatin a in multiple myeloma cells. Cancer Res. Jan. 1, 2008; 68(1):44-54.

43. Totzke G, Essmann F, Pohlmann S, Lindenblatt C, Janicke R U, Schulze-Osthoff K. A novel member of the IkappaB family, human IkappaB-zeta, inhibits transactivation of p65 and its DNA binding. J Biol Chem. May 5, 2006; 281(18):12645-12654.

44. Yamazaki S, Muta T, Takeshige K. A novel IkappaB protein, IkappaB-zeta, induced by proinflammatory stimuli, negatively regulates nuclear factor-kappaB in the nuclei. J Biol Chem. Jul. 20, 2001; 276(29):27657-27662.

45. Wu Z, Zhang X, Yang J, et al. Nuclear protein IkappaB-zeta inhibits the activity of STAT3. Biochem Biophys Res Commun. Sep. 18, 2009; 387(2):348-352.

46. Jourdan M, Veyrune J L, Vos J D, Redal N, Couderc G, Klein B. A major role for Mcl-1 antiapoptotic protein in the IL-6-induced survival of human myeloma cells. Oncogene. 2003; 22(19):2950-2959.

47. Hartl M, Nist A, Khan M I, Valovka T, Bister K. Inhibition of Myc-induced cell transformation by brain acid-soluble protein 1 (BASP1). Proc Natl Acad Sci USA. Apr. 7, 2009; 106(14):5604-5609.

48. Annunziata C M, Davis R E, Demchenko Y, et al. Frequent engagement of the classical and alternative NF-kappaB pathways by diverse genetic abnormalities in multiple myeloma. Cancer Cell. August 2007; 12(2):115-130.

49. Keats J J, Fonseca R, Chesi M, et al. Promiscuous mutations activate the noncanonical NF-kappaB pathway in multiple myeloma. Cancer Cell. August 2007; 12(2):131-144.

50. Larocque D, Galarneau A, Liu H N, Scott M, Almazan G, Richard S. Protection of p27(Kip1) mRNA by quaking RNA binding proteins promotes oligodendrocyte differentiation. Nat Neurosci. January 2005; 8(1):27-33.

51. Yang G, Fu H, Zhang J, et al. RNA-binding protein quaking, a critical regulator of colon epithelial differentiation and a suppressor of colon cancer. Gastroenterology. January 2010; 138(1):231-240 e231-235.

52. Yang G, Lu X, Wang L, et al. E2F1 and RNA binding protein QKI comprise a negative feedback in the cell cycle regulation. Cell Cycle. Aug. 15, 2011; 10(16):2703-2713.

53. Moreaux J, Reme T, Leonard W, Veyrune J L, Requirand G, Goldschmidt H, Hose D, Klein B. Gene expression-based prediction of myeloma cell sensitivity to histone deacetylase inhibitors. Br J Cancer. 2013 Aug. 6; 109(3):676-85.

The invention claimed is:

1. A method for the treatment of multiple myeloma in a patient in need thereof comprising the steps of:
   a) testing whether the patient will respond or not to a histone deacetylase inhibitor (HDACi) by performing a method comprising
      i) determining the expression level (ELi) of all genes $G_1$-$G_{37}$ in a biological sample obtained from said patient, wherein genes $G_1$-$G_{37}$ consist of SCN3A, ANK3, APLP2, QKI, SYT11, KIAA1324L, DHRS2, DFNA5, STAT1, SERPINI1, BBS9 (or PTHB1), RGS1, HLA-DPA1, FN1, KLHL24, HLA-DRA, PTPRG, RASGEF1B, OAS1, TRIM38, SERPINB1, TRPS1, CFHR1 (or CFHL1), PHLDA1, HLA-DQB1, SELL, HLA-DRB1, NFKBIZ, PARP14, CFI, MAN1C1, BASP1, GDAP1, EFHC1, ANXA1, RTN2 and DDX60L (or FLJ31033);
      ii) comparing the expression level (ELi) determined at step i) with a predetermined reference level (ELRi)
      iii) calculating the HAS score, using a computer, using the following formula $$HAS = \sum_{i=1}^{n} \beta i \times Ci$$

wherein $\beta i$ represent the regression $\beta$ coefficient reference value for the gene $G_i$ and Ci=1 if the expression of the gene $G_i$ (ELi) is higher than the predetermined reference level (ELRi) or Ci=−1 if the expression of the gene (ELi) is lower than or equal to the predetermined reference level (ELRi)
      iv) comparing the score HAS determined at step iii) with a predetermined reference value $HAS_R$
      and
   b) administering the histone deacetylase inhibitor, when said patient has as a score higher than the reference value $HAS_R$.

2. A method of testing whether a patient suffering from multiple myeloma will respond or not to a histone deacetylase inhibitor (HDACi), and of treating said patient, comprising:
   i) determining the expression level (ELi) of all genes $G_1$-$G_{37}$ in a biological sample obtained from said patient, wherein genes $G_1$-$G_{37}$ consist of SCN3A, ANK3, APLP2, OKI, SYT11, KIAA1324L, DHRS2, DFNA5, STAT1, SERPINI1, BBS9 (or PTHB1), RGS1, HLA-DPA1, FN1, KLHL24, HLA-DRA, PTPRG, RASGEF1B, OAS1, TRIM38, SERPINB1, TRPS1, CFHR1 (or CFHL1), PHLDA1, HLA-DQB1, SELL, HLA-DRB1, NFKBIZ, PARP14, CFI, MAN1C1, BASP1, GDAP1, EFHC1, ANXA1, RTN2 and DDX60L (or FLJ31033);
   ii) comparing the expression level (ELi) determined at step i) with a predetermined reference level (ELRi);
   iii) calculating the HAS score, using a computer, using the following formula $$HAS = \sum_{i=1}^{n} \beta i \times Ci$$

wherein $\beta i$ represent the regression $\beta$ coefficient reference value for the gene $G_1$ and Ci=1 if the expression of the gene $G_1$ (ELi) is higher than the predetermined reference level (ELRi) or Ci=−1 if the expression of the gene (ELi) is lower than or equal to the predetermined reference level (ELRi);
   iv) comparing the HAS score determined at step iii) with a predetermined reference value $HAS_R$;
   v) concluding that the patient will respond to the HDACi when the HAS score is higher than the predetermined reference value $HAS_R$ or concluding that the patient will not respond to the HDACi when the HAS score is lower than the predetermined reference value $HAS_R$, and
   vi) administering the HDACi when said patient has a HAS score higher than the reference value $HAS_R$.

* * * * *